United States Patent
Kranz

(10) Patent No.: US 12,234,294 B2
(45) Date of Patent: Feb. 25, 2025

(54) PHARMACEUTICAL COMPOSITION OF A HUMANIZED ANTI-CD40 ANTIBODY

(71) Applicant: Kiniksa Pharmaceuticals, GmbH, Zug (CH)

(72) Inventor: James Kranz, Lexington, MA (US)

(73) Assignee: Kiniksa Pharmaceuticals, GmbH, Zug (CH)

( * ) Notice: Subject to any disclaimer, the term of this patent is extended or adjusted under 35 U.S.C. 154(b) by 0 days.

(21) Appl. No.: 18/051,833

(22) Filed: Nov. 1, 2022

(65) Prior Publication Data

US 2023/0203179 A1 Jun. 29, 2023

Related U.S. Application Data

(60) Provisional application No. 63/276,388, filed on Nov. 5, 2021.

(51) Int. Cl.
| | |
|---|---|
| C07K 16/28 | (2006.01) |
| A61K 9/00 | (2006.01) |
| A61K 39/395 | (2006.01) |
| A61K 47/18 | (2017.01) |

(52) U.S. Cl.
CPC ........ *C07K 16/2878* (2013.01); *A61K 9/0019* (2013.01); *A61K 39/39591* (2013.01); *A61K 47/183* (2013.01); *C07K 2317/24* (2013.01); *C07K 2317/56* (2013.01)

(58) Field of Classification Search
CPC ............ C07K 16/2878; C07K 2317/24; C07K 2317/56; A61K 9/0019; A61K 39/39591; A61K 47/183
See application file for complete search history.

(56) References Cited

U.S. PATENT DOCUMENTS

| | | |
|---|---|---|
| 5,225,539 A | 7/1993 | Winter |
| 5,677,165 A | 10/1997 | de Boer et al. |
| 5,693,761 A | 12/1997 | Queen et al. |
| 5,693,762 A | 12/1997 | Queen et al. |
| 5,801,227 A | 9/1998 | Fanslow, III et al. |
| 5,874,082 A | 2/1999 | de Boer |
| 6,004,552 A | 12/1999 | de Boer et al. |
| 6,051,228 A | 4/2000 | Aruffo et al. |
| 6,054,297 A | 4/2000 | Carter et al. |
| 6,056,959 A | 5/2000 | de Boer et al. |
| 6,132,978 A | 10/2000 | Gelfand et al. |
| 6,280,957 B1 | 8/2001 | Sayegh et al. |
| 6,312,693 B1 | 11/2001 | Aruffo et al. |
| 6,315,998 B1 | 11/2001 | de Boer et al. |
| 6,413,514 B1 | 7/2002 | Aruffo et al. |
| 6,632,927 B2 | 10/2003 | Adair et al. |
| 7,063,845 B2 | 6/2006 | Mikayama et al. |
| 7,193,064 B2 | 3/2007 | Mikayama et al. |
| 7,288,251 B2 | 10/2007 | Bedian et al. |
| 7,361,345 B2 | 4/2008 | de Boer et al. |
| 7,445,780 B2 | 11/2008 | Chu et al. |
| 7,498,032 B2 | 3/2009 | Siegall et al. |
| 7,537,763 B2 | 5/2009 | Mikayama et al. |
| 7,790,166 B2 | 9/2010 | de Boer et al. |
| 8,106,164 B2 | 1/2012 | Gellerfors et al. |
| 8,138,134 B2 | 3/2012 | Zhang et al. |
| 8,226,952 B2 | 7/2012 | Thomas, Jr. et al. |
| 8,277,810 B2 | 10/2012 | Long et al. |
| 8,303,955 B2 | 11/2012 | Presta et al. |
| 8,435,514 B2 | 5/2013 | Perrin et al. |
| 8,591,900 B2 | 11/2013 | Barrett et al. |
| 8,784,823 B2 | 7/2014 | Burkly et al. |
| 8,828,396 B2 | 9/2014 | Heusser et al. |
| 8,911,726 B2 | 12/2014 | Takahashi et al. |
| 9,023,360 B2 | 5/2015 | Takahashi et al. |
| 9,023,361 B2 | 5/2015 | Takahashi et al. |
| 9,125,893 B2 | 9/2015 | Endo et al. |
| 9,475,879 B2 | 10/2016 | Suri et al. |
| 9,598,494 B2 | 3/2017 | Takahashi et al. |
| 9,974,855 B2 | 5/2018 | Yu et al. |
| 9,987,356 B2 | 6/2018 | Reimann et al. |
| 10,201,608 B2 | 2/2019 | Yu et al. |
| 10,561,728 B2 | 2/2020 | Reimann et al. |
| 10,772,958 B2 | 9/2020 | Yu et al. |
| 11,439,706 B2 | 9/2022 | Yu et al. |
| 2002/0031512 A1 | 3/2002 | Pasch et al. |
| 2003/0211100 A1 | 11/2003 | Bedian et al. |
| 2004/0110226 A1 | 6/2004 | Lazar et al. |
| 2004/0120948 A1 | 6/2004 | Mikayama et al. |
| 2005/0118166 A1 | 6/2005 | Yellin et al. |
| 2007/0110754 A1 | 5/2007 | Long et al. |

(Continued)

FOREIGN PATENT DOCUMENTS

| | | |
|---|---|---|
| CN | 103596593 A | 2/2014 |
| EP | 1297017 A2 | 4/2003 |

(Continued)

OTHER PUBLICATIONS

Strickley RG, Lambert WJ. A review of Formulations of Commercially Available Antibodies. J Pharm Sci. Jul. 2021; 110(7):2590-2608.e56. doi: 10.1016/j.xphs.2021.03.017. Epub Mar. 28, 2021. PMID: 33789155. (Year: 2021).*
Kheddo P, Tracka M, Armer J, Dearman RJ, Uddin S, van der Walle CF, Golovanov AP. The effect of arginine glutamate on the stability of monoclonal antibodies in solution. Int J Pharm. Oct. 1, 2014;473(1-2):126-33. (Year: 2014).*
Kang J, Lin X, Penera J. Rapid formulation development for monoclonal antibodies. BioProcess Technical. Apr. 2016. 14(4). (Year: 2016).*
Bramham JE, Davies SA, Podmore A, Golovanov AP. Stability of a high-concentration monoclonal antibody solution produced by liquid-liquid phase separation. MAbs. Jan.-Dec. 2021;13(1):1940666. doi: 10.1080/19420862.2021.1940666. PMID: 34225583; PMCID:

(Continued)

*Primary Examiner* — Hong Sang
*Assistant Examiner* — Carol Ann Chase
(74) *Attorney, Agent, or Firm* — Clark & Elbing LLP

(57) ABSTRACT

The present disclosure features a pharmaceutical formulation containing an anti-CD40 antibody, KPL-404.

8 Claims, 18 Drawing Sheets

Specification includes a Sequence Listing.

(56) References Cited

U.S. PATENT DOCUMENTS

| | | |
|---|---|---|
| 2007/0190051 A1 | 8/2007 | Bedian et al. |
| 2007/0218060 A1 | 9/2007 | Long et al. |
| 2008/0085531 A1 | 4/2008 | Den Hartog et al. |
| 2009/0123466 A1 | 5/2009 | Mikayama et al. |
| 2009/0202531 A1 | 8/2009 | Aukerman et al. |
| 2009/0304706 A1* | 12/2009 | Lu .................... A61P 17/06 424/144.1 |
| 2009/0311268 A1 | 12/2009 | Thomas et al. |
| 2010/0098694 A1 | 4/2010 | Bedian et al. |
| 2010/0234578 A1 | 9/2010 | Mikayama et al. |
| 2010/0239575 A1 | 9/2010 | Banchereau et al. |
| 2011/0027276 A1 | 2/2011 | Bernett et al. |
| 2011/0243932 A1 | 10/2011 | Barrett et al. |
| 2012/0121585 A1 | 5/2012 | Heusser et al. |
| 2013/0323267 A1 | 12/2013 | Endo et al. |
| 2014/0093497 A1 | 4/2014 | Reimann et al. |
| 2015/0110783 A1 | 4/2015 | Lu et al. |
| 2018/0078640 A1 | 3/2018 | Yu et al. |
| 2018/0280507 A1 | 10/2018 | Yu et al. |
| 2018/0344845 A1 | 12/2018 | Reimann et al. |
| 2019/0117771 A1 | 4/2019 | Yu et al. |
| 2020/0261547 A1 | 8/2020 | Kost et al. |
| 2020/0384107 A1 | 12/2020 | Yu et al. |
| 2021/0079093 A1 | 3/2021 | Willingham et al. |
| 2022/0133887 A1 | 5/2022 | Reimann et al. |
| 2022/0387587 A1 | 12/2022 | Yu et al. |
| 2023/0183367 A1 | 6/2023 | Paolini et al. |
| 2023/0279135 A1 | 9/2023 | Kranz |
| 2023/0287132 A1 | 9/2023 | Paolini et al. |

FOREIGN PATENT DOCUMENTS

| | | |
|---|---|---|
| EP | 1682180 A2 | 7/2006 |
| EP | 1707627 A1 | 10/2006 |
| EP | 1682180 B1 | 11/2009 |
| EP | 1297017 B1 | 6/2012 |
| EP | 1945260 B1 | 10/2012 |
| JP | 2005-508176 A | 3/2005 |
| JP | 2007-513073 A | 5/2007 |
| JP | 2009-513712 A | 4/2009 |
| JP | 2011-503098 A | 1/2011 |
| WO | WO-01/98357 A2 | 12/2001 |
| WO | WO-03/040170 A2 | 5/2003 |
| WO | WO-2005/044307 A2 | 5/2005 |
| WO | WO-2005/044854 A2 | 5/2005 |
| WO | WO-2007/053661 A2 | 5/2007 |
| WO | WO-2007/053767 A1 | 5/2007 |
| WO | WO-2007/075326 A2 | 7/2007 |
| WO | WO-2008/118356 A2 | 10/2008 |
| WO | WO-2009/062054 A1 | 5/2009 |
| WO | WO-2010/065819 A1 | 6/2010 |
| WO | WO-2012/065950 A1 | 5/2012 |
| WO | WO-2012/125569 A2 | 9/2012 |
| WO | WO-2013/164789 A2 | 11/2013 |
| WO | WO-2014/121099 A1 | 8/2014 |
| WO | WO-2016/119909 A1 | 8/2016 |
| WO | WO-2016/126702 A1 | 8/2016 |
| WO | WO-2017/004006 A1 | 1/2017 |
| WO | WO-2017040932 A1 * | 3/2017 ........... A61K 31/436 |
| WO | WO-2020/078453 A1 | 4/2020 |
| WO | WO-2023/044048 A1 | 3/2023 |

OTHER PUBLICATIONS

PMC8265796. (Year: 2021).*
U.S. Appl. No. 18/051,764, Paolini et al.
U.S. Appl. No. 18/051,807, Kranz.
U.S. Appl. No. 18/152,519, Paolini et al.
Adams et al., "Development of a chimeric anti-CD40 monoclonal antibody that synergizes with LEA29Y to prolong islet allograft survival," J Immunol. 174(1):542-50 (2005) (10 pages).
Albach et al., "Safety, pharmacokinetics, and pharmacodynamics of single rising doses of BI 655064, an antagonistic anti-CD40 antibody in healthy subjects: a potential novel treatment for autoimmune disease," Eur J Clin Pharmacol. 74(2):161-169 (2018).
Almagro et al., "Humanization of antibodies," Front Biosci. 13:1619-33 (2008).
Aoyagi et al., "A human anti-CD40 monoclonal antibody, 4D11, for kidney transplantation in cynomolgus monkeys: induction and maintenance therapy," Am J Transplant. 9(8):1732-41 (2009).
Apexigen Inc., APX005M Briefing Materials, Oncologic Drugs Advisory Committee, Jun. 21, 2017 (22 pages).
Badell et al., "Nondepleting anti-CD40-based therapy prolongs allograft survival in nonhuman primates," Am J Transplant. 12(1):126-35 (2012).
Bankert et al., "Induction of an altered CD40 signaling complex by an antagonistic human monoclonal antibody to CD40," J Immunol. 194(9):4319-27 (2015).
Boon et al., "Preclinical assessment of anti-CD40 Mab 5D12 in cynomolgus monkeys," Toxicology. 174(1):53-65 (2002).
Boon et al., "Prevention of experimental autoimmune encephalomyelitis in the common marmoset (*Callithrix jacchus*) using a chimeric antagonist monoclonal antibody against human CD40 is associated with altered B cell responses," J Immunol. 167(5):2942-9 (2001) (9 pages).
Carpenter et al., "Activation of human B cells by the agonist CD40 antibody CP-870,893 and augmentation with simultaneous toll-like receptor 9 stimulation," J Transl Med. 7:93 (2009) (10 pages).
Carter et al., "Humanization of an anti-p185HER2 antibody for human cancer therapy," Proc Natl Acad Sci U.S.A. 89(10):4285-9 (1992).
Chamberlain et al., "Repeated administration of dapirolizumab pegol in a randomised phase I study is well tolerated and accompanied by improvements in several composite measures of systemic lupus erythematosus disease activity and changes in whole blood transcriptomic profiles," Ann Rheum Dis. 76(11): 1837-44 (2017) (9 pages).
Chen et al., "Enhancement and destruction of antibody function by somatic mutation: unequal occurrence is controlled by V gene combinatorial associations," EMBO J. 14(12):2784-94 (1995).
Colman, "Effects of amino acid sequence changes on antibody-antigen interactions," Res Immunol. 145(1):33-6 (1994).
Communication and substantive Office Action for European Patent Application No. 12758099.1, dated Dec. 22, 2016 (7 pages).
Communication for European Application No. 12758099.1-1412, mailed Aug. 26, 2014 (7 pages).
Cooper et al., "Platelet-associated antibodies, cellular immunity and FCGR3a genotype influence the response to rituximab in immune thrombocytopenia," Br J Haematol. 158(4):539-47 (2012).
Cordoba et al., "A novel, blocking, Fc-silent anti-CD40 monoclonal antibody prolongs nonhuman primate renal allograft survival in the absence of B cell depletion," Am J Transplant. 15(11):2825-36 (2015).
D'Angelo et al., "Many Routes to an Antibody Heavy-Chain CDR3: Necessary, Yet Insufficient, for Specific Binding," Front Immunol. 9:395 (2018) (13 pages).
Daniluk et al., "SAT0147 Safety and Efficacy of BI 655064, An Antagonistic Anti-CD40 Antibody in Rheumatoid Arthritis (RA) Patients," Ann Rheum Dis. 75(suppl 2) (2016) (3 pages) (Abstract only).
De Boer et al., "Generation of monoclonal antibodies to human lymphocyte cell surface antigens using insect cells expressing recombinant proteins," J Immunol Methods. 152(1):15-23 (1992).
Denton et al., "Central role for CD40/CD40 ligand (CD154) interactions in transplant rejection," Pediatr Transplant. 2(1):6-15 (1998) (1 page). Abstract Only. Retrieved from <http://www.ncbi.nlm.nih.gov/pubmed/10084754> on Nov. 18, 2013.
Extended European Search Report for European Application No. 16843066.8, dated Apr. 26, 2018 (12 pages).
Extended European Search Report for European Application No. 19156093.7, mailed Sep. 25, 2019 (8 pages).
Extended European Search Report for European Patent Application No. 21156562.7 dated Oct. 8, 2021 (13 pages).
Extended European Search Report for European Patent Application No. 16843066.8, dated Apr. 26, 2018 (11 pages).

(56) References Cited

OTHER PUBLICATIONS

Final Rejection for Japanese Application No. 2013-557941, dated Mar. 7, 2017 (10 pages).
First Examination Report for Australian Patent Application No. 2012229236, issued May 4, 2016 (4 pages).
First Examination Report for Australian Patent Application No. 2016315873, dated Mar. 30, 2022 (3 pages).
First Examination Report for Australian Patent Application No. 2017216556, issued Nov. 30, 2018 (6 pages).
Fourth Office Action for Chinese Application No. 201280022277.3, issued Dec. 2, 2015 (8 pages).
Gershoni et al., "Epitope mapping—the first step in developing epitope-based vaccines," BioDrugs. 21(3):145-56 (2007).
Gilson et al., "Anti-CD40 monoclonal antibody synergizes with CTLA4-Ig in promoting long-term graft survival in murine models of transplantation," J Immunol. 183(3):1625-35 (2009) (12 pages).
Grammer et al., "Abnormal germinal center reactions in systemic lupus erythematosus demonstrated by blockade of CD154-CD40 interactions," J Clin Invest. 112(10):1506-20 (2003).
Haanstra et al., "Prevention of kidney allograft rejection using anti-CD40 and anti-CD86 in primates." Transplantation. 75(5):637-43 (2003).
International Search Report and Written Opinion for International Application No. PCT/US2012/028782, mailed Sep. 14, 2012 (11 pages).
International Search Report and Written Opinion for International Application No. PCT/US2016/050114, mailed Jan. 19, 2017 (15 pages).
Kasran et al., "Safety and tolerability of antagonist anti-human CD40 Mab ch5D12 in patients with moderate to severe Crohn's disease," Aliment Pharmacol Ther. 22(2):111-22 (2005).
Kettleborough et al., "Humanization of a mouse monoclonal antibody by CDR-grafting: the importance of framework residues on loop conformation," Protein Eng. 4(7):773-83 (1991).
Kim et al., "Costimulation blockade alters germinal center responses and prevents antibody-mediated rejection," available in PMC Apr. 14, 2014, published in final edited form as: Am J Transplant. 14(1):59-69 (2014) (19 pages).
Kim et al., "Fc-Silent Anti-CD154 Domain Antibody Effectively Prevents Nonhuman Primate Renal Allograft Rejection," available in PMC May 1, 2018, published in final edited form as: Am J Transplant. 17(5):1182-92 (2017) (24 pages).
Kussie et al., "A Single Engineered Amino Acid Substitution Changes Antibody Fine Specificity," J Immunol. 152(1):146-52 (1994).
Kuwana et al., "Effect of a single injection of humanized anti-CD154 monoclonal antibody on the platelet-specific autoimmune response in patients with immune thrombocytopenia purpura," Blood. 103(4): 1229-36 (2004) (9 pages).
Lazar et al., "A Molecular Immunology Approach to Antibody Humanization and Functional Optimization," Molecular Immunol. 44(8): 1986-98 (2007) (Abstract only) (1 page).
Lee et al., "In vitro testing of an anti-CD40 monoclonal antibody, clone 2010, in primates and pigs," available in PMC Nov. 1, 2016, published in final edited form as: Transpl Immunol. 33(3):185-191 (2015) (17 pages).
Liu et al., "Agonistic antibody to CD40 boosts the antitumor activity of adoptively transferred T cells in vivo," 35(3):276-82 (2012).
Lowe et al., "A novel monoclonal antibody to CD40 prolongs islet allograft survival," Am J Transplant. 12(8):2079-87 (2012).
Luqman et al., "The antileukemia activity of a human anti-CD40 antagonist antibody, HCD122, on human chronic lymphocytic leukemia cells," Blood. 112(3):711-20 (2008) (11 pages).
Malmborg Hager et al., "Affinity and epitope profiling of mouse anti-CD40 monoclonal antibodies," Scand J Immunol. 57(6):517-24 (2003).
Mohiuddin et al., "Role of anti-CD40 antibody-mediated costimulation blockade on non-Gal antibody production and heterotopic cardiac xenograft survival in a GTKO.hCD46Tg pig-to-baboon model," available in PMC Sep. 18, 2017, published in final edited form as: Xenotransplantation. 21(1): 35-45 (2014) (18 pages).
Mohiuddin MM, Singh AK, Corcoran PC, et al. Chimeric 2010R4 anti-CD40 antibody therapy is critical for long-term survival of GTKO.hCD46.hTBM pig-to-primate cardiac xenograft. Nat Commun. 2016;7:11138. Published Apr. 5, 2016. doi:10.1038/ncomms11138 (10 pages).
Molano et al., "Prolonged islet allograft survival in diabetic NOD mice by targeting CD45RB and CD154," Diabetes. 52(4):957-64 (2003).
Morris, Epitope mapping of protein antigens by competition ELISA. The Protein Protocols Handbook. Humana Press, 595-600 (1996).
Najafian et al., "CTLA4-Ig: a novel immunosuppressive agent," Expert Opin Investig Drugs. 9(9):2147-57 (2000).
O'Neill et al,. "Comparative Evaluation of alphaCD40 (2010R4) and alphaCD154 (5C8H1 and IDEC-131) in a Nonhuman Primate Cardiac Allotransplant Model," available in PMC Sep. 1, 2018, published in final edited form as: Transplantation. 101(9):2038-47 (2017) (22 pages).
Office Action for Canadian Patent Application No. 3,122,934, dated Jul. 25, 2022 (3 pages).
Office Action for Chinese Application No. 201280022277.3, mailed Aug. 25, 2014 (19 pages).
Office Action for Japanese Application No. 2013-557941, dated Jul. 26, 2016 (16 pages).
Office Action for Japanese Application No. 2013-557941, mailed Oct. 27, 2015 (16 pages).
Okimura et al. "Characterization of ASKP1240, a fully human antibody targeting human CD40 with potent immunosuppressive effects," Am J Transplant. 14(6):1290-99 (2014).
Oura et al., "Long-term hepatic allograft acceptance based on CD40 blockade by ASKP1240 in nonhuman primates," Am J Transplant. 12(7):1740-54 (2012).
Pearson et al., "Anti-CD40 therapy extends renal allograft survival in rhesus macaques," Transplantation. 74(7):933-40 (2002).
Piche-Nicholas et al., "Changes in Complementarity-Determining Regions Significantly Alter IgG Binding to the Neonatal Fc Receptor (FcRn) and Pharmacokinetics," MAbs. 10(1):81-94 (2018).
Queen et al., "A humanized antibody that binds to the interleukin 2 receptor," Proc Natl Acad Sci U S A. 86(24):10029-33 (1989).
Reimann, "Epitope Correction," received Aug. 14, 2017 (2 pages).
Roguska et al., "Humanization of murine monoclonal antibodies through variable domain resurfacing," Proc Natl Acad Sci U.S.A. 91(3):969-73 (1994).
Rudikoff et al., "Single amino acid substitution altering antigen-binding specificity," Proc Natl Acad Sci U S A. 79(6):1979-83 (1982).
Russo et al., "Platelet-activating factor mediates CD40-dependent angiogenesis and endothelial- smooth muscle cell interaction," J Immunol. 171(10):5489-97 (2003) (10 pages).
Schwabe et al., "FRI0168 Safety, Tolerability, Pharmacokinetics (PK) and Pharmacodynamics (PD) of BI 655064, An Antagonistic Anti-CD40 Antibody in Healthy Volunteers," Ann Rheum Dis. 74(suppl 2) (2015) (3 pages) (Abstract only).
Second Office Action for Chinese Application No. 201280022277.3, issued Mar. 24, 2015 (12 pages).
Sho et al., "Requirements for induction and maintenance of peripheral tolerance in stringent allograft models," Proc Natl Acad Sci USA. 102(37):13230-5 (2005).
Shock et al., "CDP7657, an anti-CD40L antibody lacking an Fc domain, inhibits CD40L-dependent immune responses without thrombotic complications: an in vivo study," Arthritis Res Ther. 17:234 (2015) (12 pages).
Slade et al., "Assessment of Safety, Pharmacokinetics and Pharmacodynamics of a Novel Anti-CD40 Monoclonal Antibody, CFZ533, in Healthy Volunteers and in Rheumatoid Arthritis Patients," 2016 ACR/ARHP Annual Meeting, Nov. 11-16, Washington, DC. 68 (suppl 10), Abstract 1582 (2016) (2 pages).
Strohl, "Optimization of Fc-mediated effector functions of monoclonal antibodies," Curr Opin Biotechnol. 20(6):685-91 (2009).
Sutherland et al., "Anti-CD45RB antibody deters xenograft rejection by modulating T cell priming and homing," Int Immunol. 14(8):953-62 (2002).

(56) References Cited

OTHER PUBLICATIONS

Third Office Action for Chinese Application No. 201280022277.3, issued Aug. 24, 2015 (10 pages).
Thompson et al., "CD40-specific costimulation blockade enhances neonatal porcine islet survival in nonhuman primates," Am J Transplant. 11(5):947-57 (2011).
Visvanathan et al., "FRI0231 Treatment with BI 655064 (Antagonistic Anti-CD40 Antibody) Modulates Biomarkers Associated with Rheumatoid Arthritis (RA)," Ann Rhem Dis. 75(suppl 2) (2016) (3 pages) (Abstract only).
Visvanathan et al., "Treatment with BI 655064 (Antagonistic Anti-CD40 Antibody) Modulates Clinical and Biomarker Parameters Associated with Rheumatoid Arthritis (RA)," Scientific Abstracts, p. 517 Jun. 10, 2016.
Vonderheide et al., "Agonistic CD40 Antibodies and Cancer Therapy," Clin Cancer Res. 19(5):1035-1043 (2013) (10 pages).
Winter et al., "Humanized antibodies," Trends Pharmacol Sci. 14(5):139-43 (1993).
Wu, Chapter 12: Simultaneous Humanization and Affinity Optimization of Monoclonal Antibodies. *Methods in Molecular Biology, vol. 207: Recombinant Antibodies for Cancer Therapy: Methods and Protocols*. Humana Press Inc., 197-212 (2003).
Yamniuk et al., "Functional Antagonism of Human CD40 Achieved by Targeting a Unique Species-Specific Epitope," J Mol Biol. 428(14):2860-79 (2016).
International Search Report and Written Opinion for PCT/US2022/079072, mailed Feb. 8, 2023 (23 pages).
International Search Report and Written Opinion for PCT/US2023/060358, dated May 30, 2023 (16 pages).
*Amgen, Inc.*, Petitioner v. *Abbvie Biotechnology Ltd.*, Patent Owner, Case IPR2015-01514, U.S. Pat. No. 8,916,157 B2, Entered: Jan. 14, 2015 (25 pages).
Wang et al., "Antibody structure, instability, and formulation," J Pharm Sci. 96(1): 1-26 (Jan. 2007).
Genovese et al., "Efficacy and Safety of ABT-494, a Selective JAK-1 Inhibitor, in a Phase IIb Study in Patients With Rheumatoid Arthritis and an Inadequate Response to Methotrexate," Arthritis Rheumatol. 68(12):2857-2866 (Dec. 2016).
Visvanathan et al., "Effects of BI 655064, an antagonistic anti-CD40 antibody, on clinical and biomarker variables in patients with active rheumatoid arthritis: a randomised, double-blind, placebo-controlled, phase IIa study," Ann Rheum Dis. 78(6):754-760 (Jun. 2019) (Epub Mar. 22, 2019).
Extended European Search Report for European Patent Application No. 23212999.9, dated Apr. 16, 2024 (9 pages).
Margolis et al., "Long-acting antiviral agents for HIV treatment," Curr Opin HIV AIDS. 10(4):246-52 (Jul. 2015).
Moel et al., "In rheumatoid arthritis, changes in autoantibody levels reflect intensity of immunosuppression, not subsequent treatment response", Arthritis Research & Therapy. 21:28 (Jan. 2019) (8 pages).
Wilson, "Rheumatoid factors in patients with rheumatoid arthritis", Canadian Family Physician. 52 (Feb. 2006) (2 pages).
Bruns et al, "Prospective cohort study of effects of infliximab on rheumatoid factor, anti-cyclic citrullinated peptide antibodies and antinuclear antibodies in patients with long-standing rheumatoid arthritis", Joint Bone Spine. 76:248-253 (Feb. 2009).

\* cited by examiner

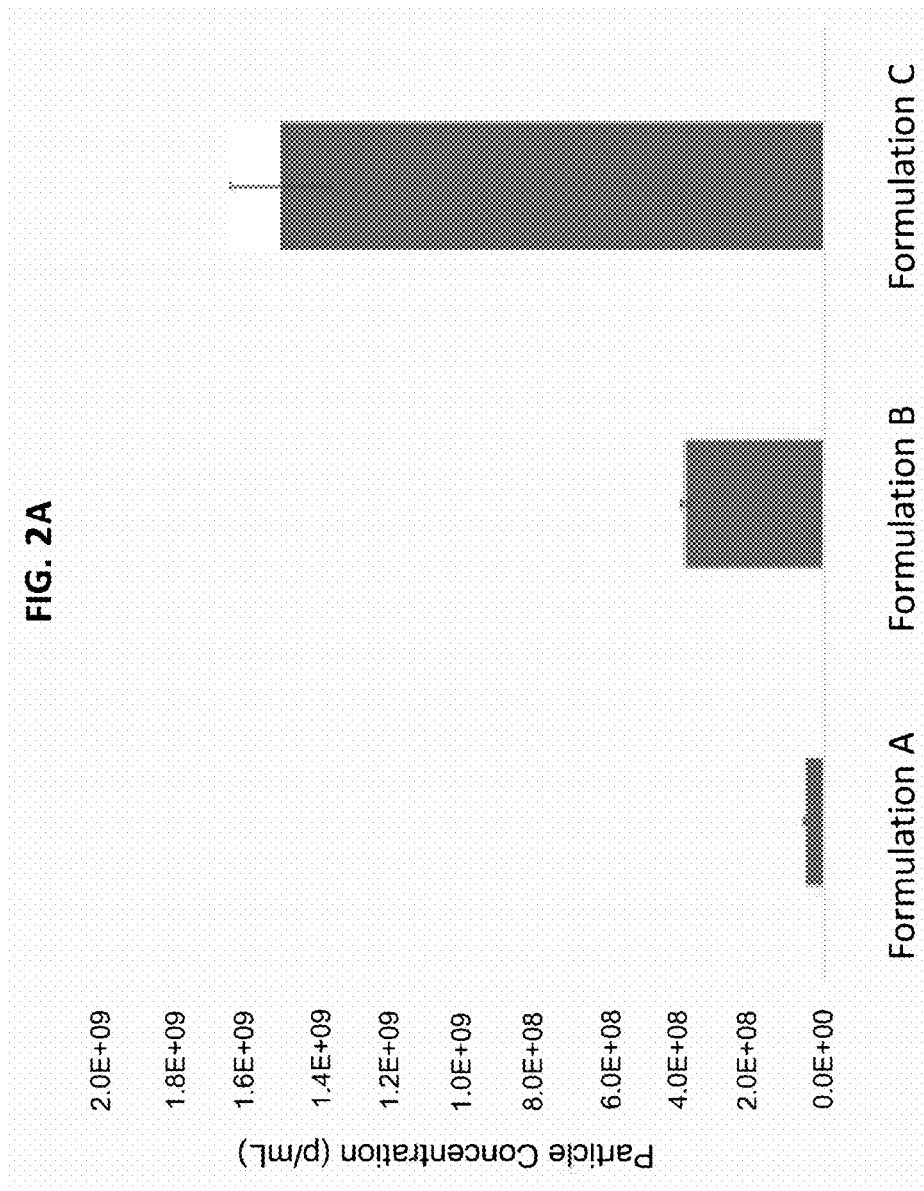

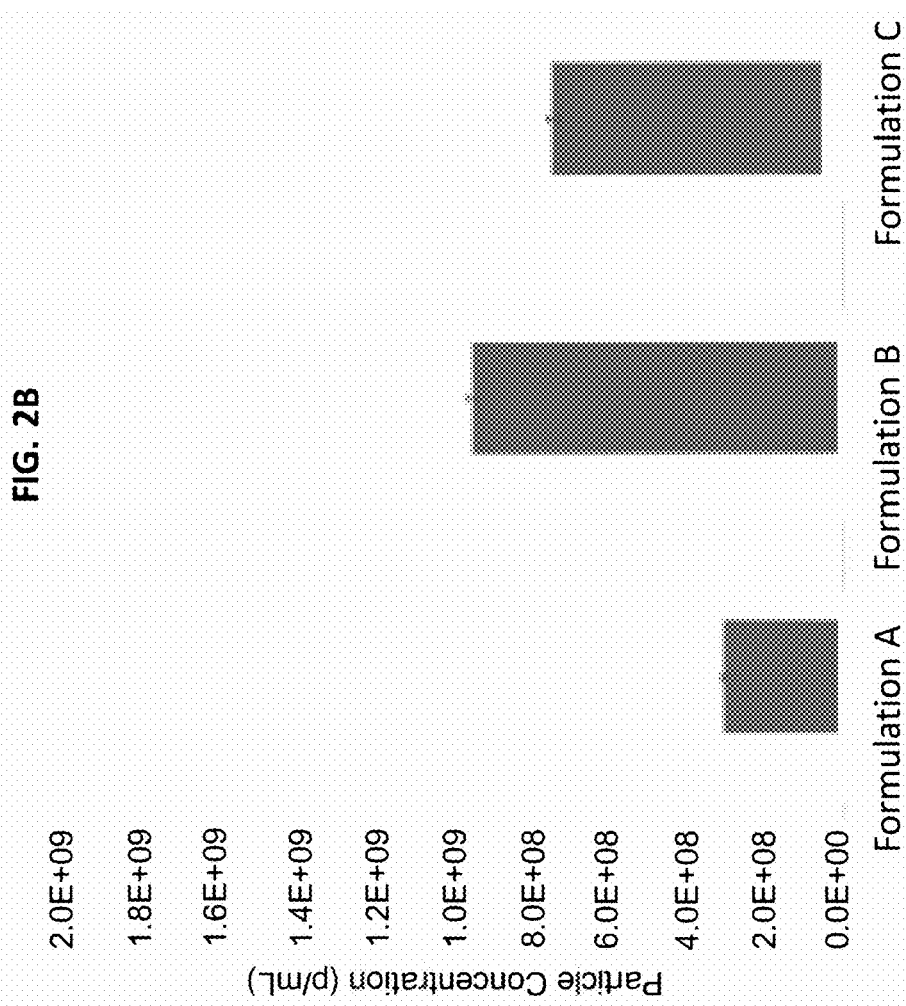

```
SEQUENCE LISTING

Sequence total quantity: 2
SEQ ID NO: 1              moltype = AA   length = 441
FEATURE                   Location/Qualifiers
source                    1..441
                          mol_type = protein
                          organism = Homo sapiens
SEQUENCE: 1
QVQLVQSGAE VKKPGASVKV SCKASGYTFT NYWMHWVRQA PGQRLEWIGY INPSNDYTKY    60
NQKFKDRATL TADKSANTAY MELSSLRSED TAVYYCARQG FPYWGQGTLV TVSSASTKGP   120
SVFPLAPCSR STSESTAALG CLVKDYFPEP VTVSWNSGAL TSGVHTFPAV LQSSGLYSLS   180
```

```
SVVTVPSSSL GTKTYTCNVD HKPSNTKVDK RVESKYGPPC PPCPAPEFLG GPSVFLFPPK    240
PKDTLMISRT PEVTCVVVDV SQEDPEVQFN WYVDGVEVHN AKTKPREEQF NSTYRVVSVL    300
TVLHQDWLNG KEYKCKVSNK GLPSSIEKTI SKAKGQPREP QVYTLPPSQE EMTKNQVSLT    360
CLVKGFYPSD IAVEWESNGQ PENNYKTTPP VLDSDGSFFL YSRLTVDKSR WQEGNVFSCS    420
VMHEALHNHY TQKSLSLSPG K                                              441

SEQ ID NO: 2           moltype = AA  length = 213
FEATURE                Location/Qualifiers
source                 1..213
                       mol_type = protein
                       organism = Homo sapiens
SEQUENCE: 2
EIVLTQSPAT LSLSPGERAT LSCSASSSVS YMHWYQQKPG QAPRRWIYDT SKLASGVPAR    60
FSGSGSGTDY TLTISSLEPE DFAVYYCHQL SSDPFTFGGG TKVEIKRTVA APSVFIFPPS    120
DEQLKSGTAS VVCLLNNFYP REAKVQWKVD NALQSGNSQE SVTEQDSKDS TYSLSSTLTL    180
SKADYEKHKV YACEVTHQGL SSPVTKSFNR GEC                                 213
```

PHARMACEUTICAL COMPOSITION OF A HUMANIZED ANTI-CD40 ANTIBODY

SEQUENCE LISTING

This application contains a Sequence Listing which has been filed electronically in Extensible Markup Language (XML) format and is hereby incorporated by reference in its entirety. Said XML copy, created on Oct. 28, 2022, is named 51383-004002_Sequence_Listing_10_28_22.XML and is 3,277 bytes in size.

BACKGROUND

Suppression of the immune system, particularly the humoral immune system, is beneficial in organ transplantation and treatment of autoimmune disorders.

One target for suppressing the immune system is the CD40/CD154 interaction. CD40 is expressed primarily on the surface of B lymphocytes and other antigen-presenting cells (APCs) such as dendritic cells and macrophages. CD154 is expressed primarily on the surface of T cells. The interaction between these two proteins is associated with B cell activation, which triggers cytokine expression as well as expression of cell surface markers including CD23, CD80, and CD86. Antibodies (e.g., humanized antibodies) that target the CD40/CD154 interaction have been developed. There exists a need for pharmaceutical formulations suitable for preparing and administering such antibodies.

SUMMARY

In one aspect, featured is a pharmaceutical composition formulated for intravenous injection that contains 200 mg/mL of an anti-CD40 antibody with a heavy chain variable region having the amino acid sequence set forth in SEQ ID NO: 1 and a light chain variable region having the amino acid sequence set forth in SEQ ID NO: 2. The pharmaceutical composition includes 0.02% polysorbate 20, 50 mM sodium acetate, 100 mM arginine, and 100 mM glutamate, a pH of 5.4. In some embodiments, the composition is formulated in a volume of 2.0 mL. In some embodiments, at least 98% of the humanized anti-CD40 antibody is present in the composition in a monomeric form. In some embodiments, less than 2% of the humanized anti-CD40 antibody in the composition is present as a high molecular weight (HMW) species.

In another aspect, featured is a pharmaceutical composition formulated for subcutaneous injection that contains 200 mg/mL of an anti-CD40 antibody with a heavy chain variable region having the amino acid sequence set forth in SEQ ID NO: 1 and a light chain variable region having the amino acid sequence set forth in SEQ ID NO: 2. The pharmaceutical composition includes 0.02% polysorbate 20, 50 mM sodium acetate, 100 mM arginine, and 100 mM glutamate, a pH of 5.4. In some embodiments, the composition is formulated in a volume of 2.0 mL. In some embodiments, at least 98% of the humanized anti-CD40 antibody is present in the composition in a monomeric form. In some embodiments, less than 2% of the humanized anti-CD40 antibody in the composition is present as an HMW species.

In another aspect, featured is a method of suppressing the immune system in a human subject by administering to the human subject by intravenous injection of a pharmaceutical composition that contains 200 mg/mL of an anti-CD40 antibody with a heavy chain variable region having the amino acid sequence set forth in SEQ ID NO: 1 and a light chain variable region having the amino acid sequence set forth in SEQ ID NO: 2. The pharmaceutical composition includes 0.02% polysorbate 20, 50 mM sodium acetate, 100 mM arginine, and 100 mM glutamate and has a pH of 5.4. In some embodiments, the composition is formulated in a volume of 2.0 mL.

In another aspect, featured is a method of suppressing the immune system in a human subject by administering to the human subject by subcutaneous injection of a pharmaceutical composition that contains 200 mg/mL of an anti-CD40 antibody with a heavy chain variable region having the amino acid sequence set forth in SEQ ID NO: 1 and a light chain variable region having the amino acid sequence set forth in SEQ ID NO: 2. The pharmaceutical composition includes 0.02% polysorbate 20, 50 mM sodium acetate, 100 mM arginine, and 100 mM glutamate and has a pH of 5.4. In some embodiments, the composition is formulated in a volume of 2.0 mL.

BRIEF DESCRIPTION OF THE DRAWINGS

FIGS. 2A and 2B are graphs showing comparison of particle concentrations from biophysical characterization studies. FIG. 2A shows 200 mg/mL KPL-404 Formulations A-C (no PS20 in Formulation C), and FIG. 2B shows high concentrations of KPL-404 in Formulations A-C.

DETAILED DESCRIPTION

Figure 1:
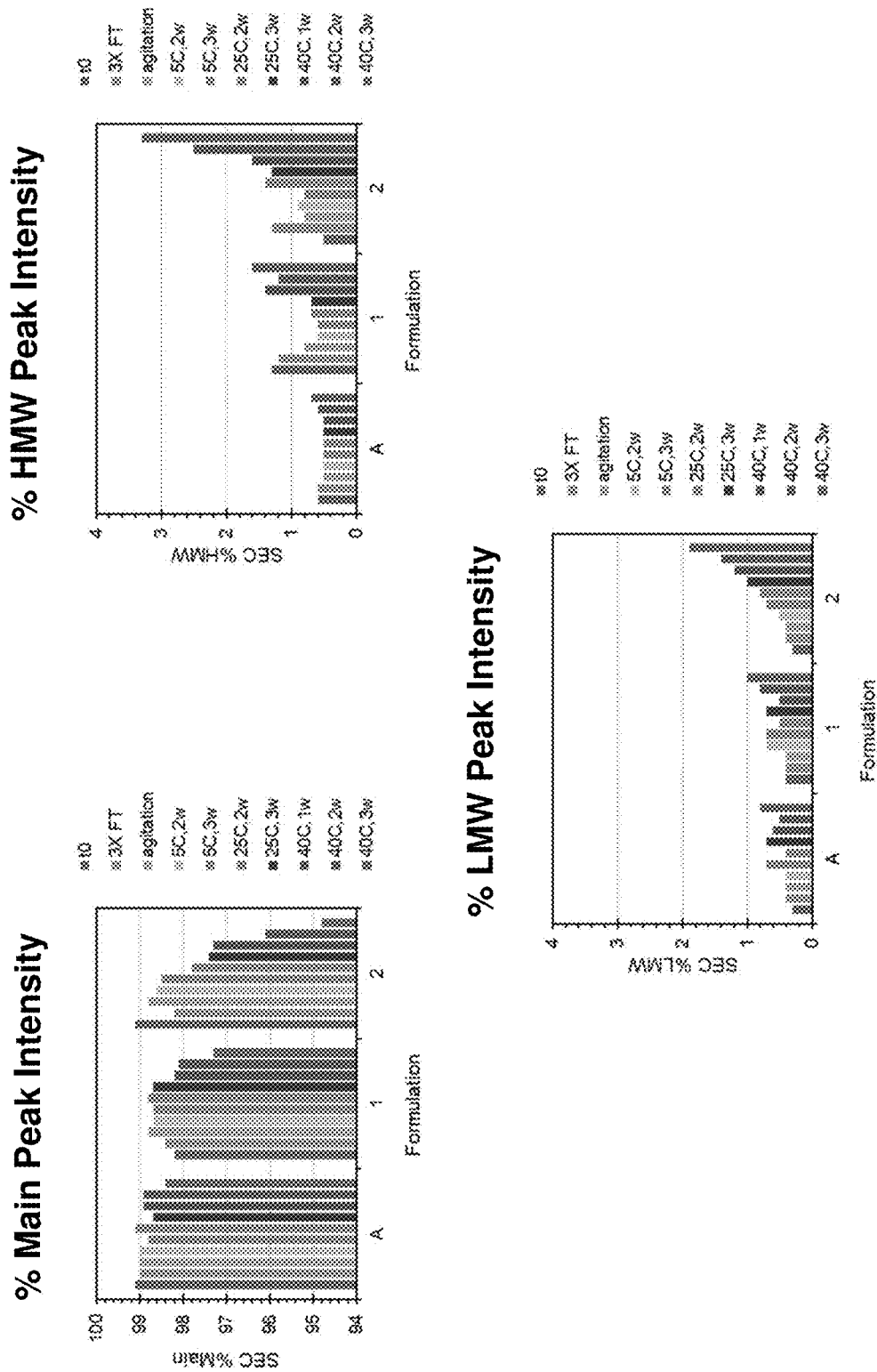
FIG. 1 is a set of graphs showing SEC results presented graphically for % Main, % HMW and % LMW species of KPL-404 for Formulations A, 1 and 2.

The present disclosure features a pharmaceutical composition containing an anti-CD40 antibody (see, e.g., PCT Pub.

Nos. WO 2012/125569 and WO 2017/040932, which are herein incorporated by reference in their entirety) at a concentration of 200 mg/mL. The composition includes 0.02% polysorbate 20, 50 mM sodium acetate, 100 mM arginine, and 100 mM glutamate, has a pH of 5.4. The composition may be present in a container in a volume of 2.0 mL. The formulation described herein contains a high concentration (as described herein) of the anti-CD40 antibody. The formulation enhances the stability of the antibody (e.g., exhibits an extended shelf-life), reduces aggregation of the antibody, and improves viscosity parameters of the composition.

Anti-CD40 Antibody

The pharmaceutical composition described herein includes an anti-CD40 antibody (KPL-404). The heavy chain of the antibody is set forth in SEQ ID NO: 1 and the light chain of the antibody is set forth in SEQ ID NO: 2.

```
KPL-404 Heavy Chain
                                           (SEQ ID NO: 1)
QVQLVQSGAEVKKPGASVKVSCKASGYTFTNYWMHWVRQAPGQRLEWIGY

INPSNDYTKYNQKFKDRATLTADKSANTAYMELSSLRSEDTAVYYCARQG

FPYWGQGTLVTVSSASTKGPSVFPLAPCSRSTSESTAALGCLVKDYFPEP

VTVSWNSGALTSGVHTFPAVLQSSGLYSLSSVVTVPSSSLGTKTYTCNVD

HKPSNTKVDKRVESKYGPPCPPCPAPEFLGGPSVFLFPPKPKDTLMISRT

PEVTCVVVDVSQEDPEVQFNWYVDGVEVHNAKTKPREEQFNSTYRVVSVL

TVLHQDWLNGKEYKCKVSNKGLPSSIEKTISKAKGQPREPQVYTLPPSQE

EMTKNQVSLTCLVKGFYPSDIAVEWESNGQPENNYKTTPPVLDSDGSFFL

YSRLTVDKSRWQEGNVFSCSVMHEALHNHYTQKSLSLSPGK

KPL-404 Light Chain
                                           (SEQ ID NO: 2)
EIVLTQSPATLSLSPGERATLSCSASSSVSYMHWYQQKPGQAPRRWIYDT

SKLASGVPARFSGSGSGTDYTLTISSLEPEDFAVYYCHQLSSDPFTFGGG

TKVEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC
```

Pharmaceutical Composition

The anti-CD40 antibody, KPL-404, can be incorporated into a formulation for intravenous injection. The pharmaceutical composition has 200 mg/mL of the anti-CD40 antibody (KPL-404), 0.02% polysorbate 20, 50 mM sodium acetate, 100 mM arginine, 100 mM glutamate, and a pH of 5.4. The composition may be present in a container with about 2.0 mL extractable volume.

The anti-CD40 antibody, 2C10, can be incorporated into a formulation for subcutaneous injection. The pharmaceutical composition can include 200 mg/mL of the anti-CD40 antibody (KPL-404), 0.02% polysorbate 20, 50 mM sodium acetate, 100 mM arginine, 100 mM glutamate, and a pH of 5.4. The composition may be present in a container with about 2.0 mL extractable volume.

Kits

The disclosure also features a kit with a container that includes, for example, 2.0 mL of the pharmaceutical composition of the anti-CD40 antibody, KPL-404, described herein. The container can include a label providing details of the composition. Suitable containers include, for example, bottles, vials, syringes, and test tubes. The containers may be formed from a variety of materials such as glass or plastic. The container holds a pharmaceutical composition as described herein and may include, e.g., a sterile access port. The composition may also be formulated in a prefilled syringe. The composition may also be formulated in an autoinjector.

For example, the container may be an intravenous solution bag or a vial having a stopper pierceable by a hypodermic injection needle. The kit may also include a second container with a pharmaceutically acceptable buffer, such as phosphate-buffered saline, Ringer's solution, and dextrose solution. The kit may include other materials, including buffers, diluents, filters, needles, syringes, and package inserts with instructions for use.

EXAMPLES

The following examples of specific aspects for carrying out the present disclosure are offered for illustrative purposes only and are not intended to limit the scope of the present disclosure in any way.

Example 1

Described herein are studies that were performed to assess formulations that would allow for an increase in the concentration of KPL-404 to at least 100 mg/mL.

Unless otherwise noted, the candidate formulations described herein include KPL-404 and the following excipients:

Formulation 1: 20 mM sodium phosphate, 200 mM glycine, 0.01% polysorbate 20 (PS20), pH 6.5

Formulation 2: 50 mM sodium Acetate/NaAcetate, 200 mM glycine 0.01% PS20, pH 5.5

Formulation A: 50 mM Acetate/NaAcetate, 7% (w/v) sucrose, 0.01% PS20, pH 5.4

Formulation B: 50 mM Acetate/NaAcetate, 2.5% (w/v) sorbitol, 70 mM NaCl, 0.01% PS20, pH 5.4

Formulation C: 50 mM Acetate/NaAcetate, 100 mM Arginine, 100 mM Glutamate, 0.01% PS20, pH 5.4

Formulation C was selected as the formulation for 200 mg/mL KPL-404 formulation for drug substance (DS) and drug product (DP) with 0.02% PS20, instead of 0.01% PS20.

Screening Studies

To evaluate the stability of KPL-404 in a formulation screen, KPL-404 was exchanged into 12 different buffers, including Formulations A (pH 5.6), 1 and 2. Freeze/Thaw (F/T) stress was assessed, cycling samples between −70 C and ambient temperature three times. Agitation stress was also assessed by shaking at 200 rpm for 48 hours in the upright position. A short-term stability study was conducted, with samples stored at 2-8° C., 25° C., or at 40° C. for up to 3 weeks. The SEC results show that the excipient does play an important role in ensuring KPL-404 stability following F/T and agitation stress, with glycine Formulations 1 and 2 being most susceptible to degradation, i.e., loss of % Main species, or increase either in % HMW or % LMW species. KPL-404 was stable in Formulation A, which included sucrose as a stabilizing agent. SEC results for screened formulations A, 1, and 2 are presented graphically in FIG. 1. There are clear differences among the formulations, with Formulation 2 being the least stable showing loss of main and increase of both HMW and LMW species. Formulation 1 showed increases in HMW species at 40° C. and unstable during F/T stress and agitation tests. Formulation A was the lead candidate in these screening studies and was selected for further development studies.

Development Studies

Following the screening studies, subsequent studies were performed in three candidate formulations that were identified as part of the development studies:

KPL-404 was formulated at 200 mg/mL in each of the three candidate formulations (Formulations A-C) by UF/DF and set on stability in a vial presentation.

KPL-404 was highly concentrated by UF/DF until the flux went to zero. The concentrations that were achieved were:

272 mg/mL KPL-404 in Formulation A: (50 mM Acetate, 7% (w/v) sucrose, 0.001% PS20, pH 5.4)

274 mg/mL KPL-404 in Formulation B: 50 mM Acetate, 2.5% (w/v) sorbitol, 70 mM NaCl, 0.001% PS20, pH 5.4

291 mg/mL KPL-404 in Formulation C: 50 mM Acetate, 100 mM Arg/100 mM Glu, 0.001% PS20, pH 5.4

Samples of each of these were characterized externally using biophysical techniques to characterize self-association as a function of protein concentrations. Drug substance material used to prepare these formulations was initially manufactured with PS20 at 0.001%. Separately, formulations were spiked with 10% (w/v) PS20 to achieve 0.01% PS20 and were also analyzed.

In parallel, CG-MALS testing was performed on formulations with PS20 adjusted to 0.01%.

Viscosity and Instron testing were performed as a function of protein concentration to assess syringeability.

From these characterization studies, it was concluded that KPL-404 could achieve a concentration of up to 292 mg/mL in Formulation C. Abbreviated stability studies were performed at 220 mg/mL each of Formulations A and B, and at 235 mg/mL in Formulation C.

We selected Formulation C at 200 mg/mL KPL-404 for both drug substance and for drug product based on its improved characteristics relative to Formulations A and B.

Materials

Material Generation for Assessing High Concentration of KPL-404

Initial Testing

Non-GMP drug substance was diluted into each of the three buffers, followed by concentration to 200 mg/mL. It was expected that the polysorbate 20 present in the DS would co-concentrate with KPL-404 in the centrifugal unit.

Material Generation for Stability Studies

UFDF Testing:

To generate load material for each ProA cycle, drug substance was thawed in a 25° C. water bath and adjusted using ProA equilibration buffer to a target 10 g/L. The conditioned ProA load material was 0.2 µm filtered prior to loading the column. Each Pro A eluate was neutralized to target pH 5.00, 0.2 µm filtered, and stored at ≤−65° C. A total of 4 cycles were performed to generate 68 grams of UFDF load material for high concentration studies.

Material Generation for UFDF Confirmation:

To generate load material for each ProA cycle, drug substance was thawed at 2-8° C. overnight and adjusted using ProA equilibration buffer to a target 10 g/L. The conditioned ProA load material was 0.2 µm filtered prior to loading the column. Each Pro A eluate was 0.2 µm filtered and stored at ≤−65° C. A total of 3 cycles were performed to generate 54 grams of UFDF load material for high concentration studies.

For each run, neutralized ProA eluate was thawed at 2-8° C., 0.2 µm filtered, and used as UFDF load. The starting material was concentrated to a target 50 g/L, diafiltered into the relevant buffer and then concentrated until a prohibitive drop in flux occurred or the retentate showed visual deterioration. During processing, when a target of 200 g/L was reached, 40 mL of the in-process pool was sampled for drug product processing. The remaining pool was then further concentrated while adjusting feed flow rate and transmembrane pressure to ensure equipment capacity was not exceeded at high concentration and high pressure.

A system rinse using 1× to 1.5× the holdup volume was performed to allow for a process step mass balance calculation. A PS20 stock solution of 10% w/v was prepared in each respective formulation buffer and spiked into both the target 200 g/L sample to a target 0.01% PS20. Final 0.2 µm filtration was performed using 3.5 cm² PES filters from Sartorius. Each pool was filtered separately, and the pressure monitored. The remainder of the drug substance pools were handled in accordance with the DP stability study to ensure compliance with that study's objectives.

Results and Discussion

Effect of Formulations A-C on >200 mg/mL KPL-404

Small scale UF/DF was performed to generate the following samples, which were concentrated until the tangential flow stopped. These were considered to be at their threshold of solubility:

Formulation A (sucrose-based, Ph1 formulation): 50 mM Acetate, 7% (w/v) sucrose, 0.01% PS20, pH 5.4—achieved 212.6 mg/mL KPL-404

Formulation B (sorbitol-based): 50 mM Acetate, 2.5% (w/v) sorbitol, 70 mM NaCl, 0.01% PS20, pH 5.4—achieved 195.5 mg/mL KPL-404

Formulation C (Arg/Glu-based): 50 mM Acetate, 100 mM Arg/100 mM Glu, 0.01% PS20, pH 5.4—achieved 214.1 mg/mL KPL-404

The study used KPL-404 drug substance (i.e., an antibody having a heavy chain with the amino acid sequence set forth in SEQ ID NO: 1, and a light chain with the amino acid sequence set forth in SEQ ID NO: 2) that was processed over a Protein-A column to remove all residual buffer components including PS20, followed by ultrafiltration/diafiltration (UFDF) into each of Formulation A, Formulation B, or Formulation C, at 200 mg/mL. The formulations were then further concentrated up to ~250 mg/mL. To all of these, PS20 was added to a target of 0.01% and then filtered.

Biophysical Characterization

Malvern Panalytical Studies

Formulations were studied by a variety of biophysical techniques, including dynamic light scattering, static light scattering (B22 and CIMax), electrophoretic light scattering (Zeff), thermodynamic stability by differential scanning calorimetry (melting transitions), injectability by microcapillary viscometry and rheology, and nanoparticle tracking analysis.

An initial set of formulations were characterized at 200 mg/mL as shown in Table 2. It was discovered that Formulation C lacked PS20 after testing had been completed.

TABLE 2

Biophysical Stability Profiles of 200 mg/mL KPL-404 Formulations

| | Developability | | | | | | Injectability | | Manufacturability | | | | SVPs |
|---|---|---|---|---|---|---|---|---|---|---|---|---|---|
| Formulation | $B_{22}$ | $R_S$ | $k_D$ | $k_D^*$ | $Z_{eff}$ | $C_{IMax}$ | $\eta_{100}$ | $\eta_{stock}$ | $T_0$ | $T_{m1}$ | $T_{m2}$ | $T_{m3}$ | $C_{sup}$ |
| A‡ | 8.9e−5 | 5.1 | −0.65 | 5.79 | 1.4 | 113 | 2.296 | 21.22 | 57.4 | 65.7 | 72.1 | 75.2 | 5.15e7 |
| B‡ | 4.4e−5 | 5.3 | −2.26 | 3.49 | 2.0 | 113 | 2.071 | 14.45 | 56.5 | 64.9 | 71.5 | 74.1 | 3.85e8 |
| C‡ | 1.8e−5 | 5.4 | −1.91 | 3.08 | 1.8 | 108 | 2.035 | 14.79 | 56.5 | 64.6 | 71.5 | 74.5 | 1.51e9 |

‡With~0.001% polysorbate 20;
*viscosity-corrected $k_D$

TABLE 3

Biophysical Stability Profiles of High Concentration KPL-404 Formulations

| | Developability | | | | | | Injectability | | Manufacturability | | | | SVPs |
|---|---|---|---|---|---|---|---|---|---|---|---|---|---|
| Formulation | $B_{22}$ | $R_S$ | $k_D$ | $k_D^*$ | $Z_{eff}$ | $C_{IMax}$ | $\eta_{100}$ | $\eta_{stock}$ | $T_0$ | $T_{m1}$ | $T_{m2}$ | $T_{m3}$ | $C_{sup}$ |
| A† | 6.9e−5 | 5.1 | −2.43 | 3.41 | N.T. | 113 | 2.630 | 91.10 | 56.8 | 65.4 | 72.5 | 75.3 | 3.05e8 |
| B† | 4.1e−5 | 5.4 | −3.08 | 9.60 | N.T. | 113 | 3.100 | 48.20 | 53.8 | 67.2 | 73.0 | | 9.47e8 |
| C† | 7.9e−5 | 5.4 | −1.01 | 19.92 | N.T. | 108 | 2.330 | 67.10 | 56.3 | 67.7 | 73.7 | | 7.42e8 |

†With~0.02% polysorbate 20;
*viscosity-corrected $k_D$

With the formulations containing nominal levels of PS20, Formulation C had the lowest colloidal stability based on kD value. Similarly, Formulation C had the highest concentration of subvisible particles ($C_{sup}$) compared to Formulations A and B (FIG. 2A).

Thermal analysis indicated similar thermal stability for aggregation onset and for each of the three observed thermal transitions, with Formulation A being higher in stability due to sucrose, in comparison to Formulations B and C which were essentially equivalent.

Biophysical characterization studies were repeated following generation of high concentration (>200 mg/mL) KPL-404 formulations, including 0.02% PS20 in Formulation C, Table 3. When 0.02% PS20 was in the formulations, Formulation C had the highest colloidal stability based on kD value. Similarly, Formulation C had a lower concentration of subvisible particles ($C_{sup}$) compared to Formulation B (FIG. 2B).

Figure 3:
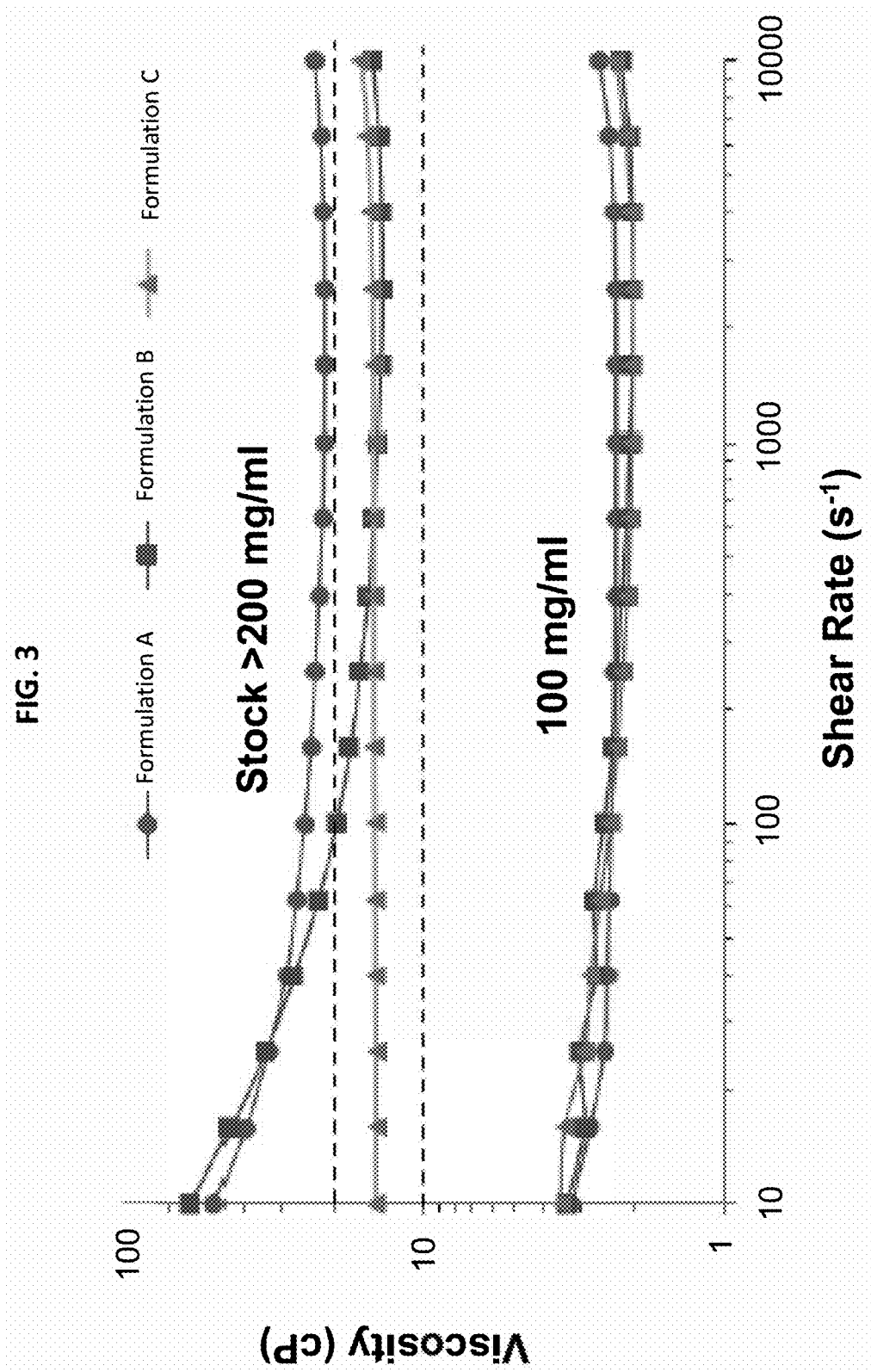
FIG. 3 is a graph showing viscosity vs. shear rate for high concentration KPL-404 formulations.

Rheological assessment of viscosity as a function of shear rate showed different behavior at 100 mg/mL and >200 mg/mL (FIG. 3).

At 100 mg/mL, all formulations demonstrated Newtonian behavior with similar viscosities as a function of shear rate. However, at >200 mg/mL a common non-Newtonian "shear-thinning" effect for Formulations A and B, but a static invariant viscosity vs shear rate is observed for Formulation C. This suggests the Arg/Glu excipients in Formulation C inhibit self-association at high concentration, whereas low energy self-associations were present at low shear-rates for Formulations A and B that were disrupted as the shear rate increases.

This behavior is consistent with a change in mechanism of colloidal stability above 250 mg/mL, wherein protein self-association becomes dominant rather than the hard sphere mixture model that is characteristic of a dilute protein solution for KPL-404 in Formulations A and B. Conversely, for KPL-404 in Formulation C, the absence of shear thinning at elevated concentrations translates to an exponential increase in viscosity as a function of protein concentration up to 292 mg/mL. The combination of arginine and glutamate stabilizes KPL-404 against self-association via a different mechanism than sucrose in Formulation A or sorbitol/NaCl in Formulation B.

In summary, biophysical characterization of KPL-404 formulations showed differences in mechanism of stabilization, with the sucrose Formulation A being less optimal than either Formulation B or C. Data suggest Formulation C may be most effective at limiting self-association at elevated concentrations through a combination of Arg/Glu and PS20.

Biophysical Studies

Concentration-gradient multiangle light scattering (CG-MALS) was employed to assess oligomeric behavior of KPL-404 over a range of concentrations. Individual samples were prepared at different concentrations and analyzed by static light scattering (SLS).

Wyatt technologies has implemented CG-MALS by merging an autosampler that generates a concentration gradient from two solutions (from a high concentration protein formulation and matched placebo) in conjunction with in-line sample analysis.

KPL-404 formulations and matching formulation buffers were filtered using 0.22 μm syringe filters. Fifteen concentrations were analyzed per formulation, with concentrations confirmed by UV Absorbance.

Fitting of data to reversible/irreversible association models were performed using Wyatt Calypso software (144 kDa monomer).

CG-MALS Results for Formulation A

Figure 4:
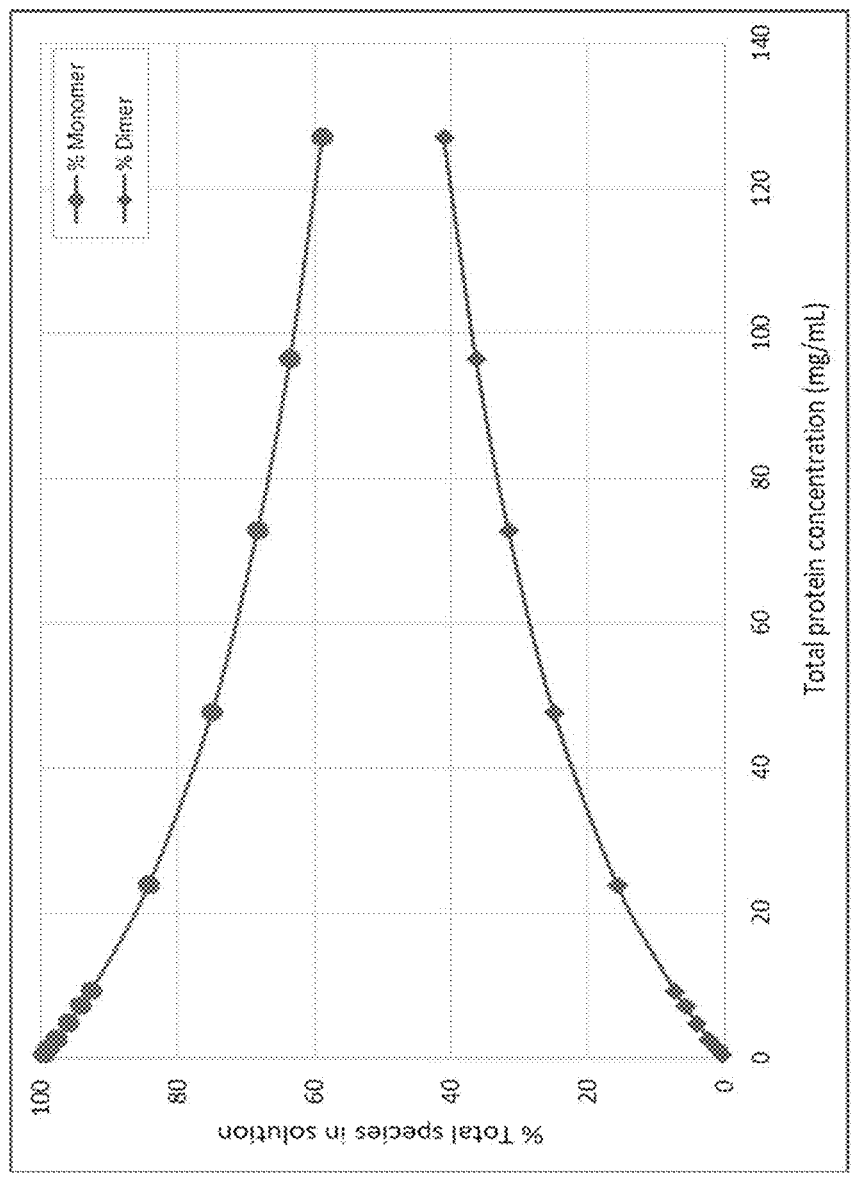
FIG. 4 is a graph showing Total KPL-404 species Population by CG-MALS for formulation A.

No reversible associations could be modeled with the highest concentration points included. The inability to fit reversible oligomers may be due to repulsive interactions at higher concentrations dominating and masking the underlying attractive interactions Due to strong repulsive interactions masking underlying attractive interactions, the highest concentration we could fit with the reversible associations model was ~127 mg/mL with reversible dimer. Data up to ~127 mg/mL could be modeled with reversible dimer. Concentration of reversible dimer did not exceed the monomer within the concentration range that we could fit. Reversible dimer was present even at the lowest concentration (~0.5 mg/mL); see FIG. 4.

CG-MALS Results for Formulation B

Figure 5:
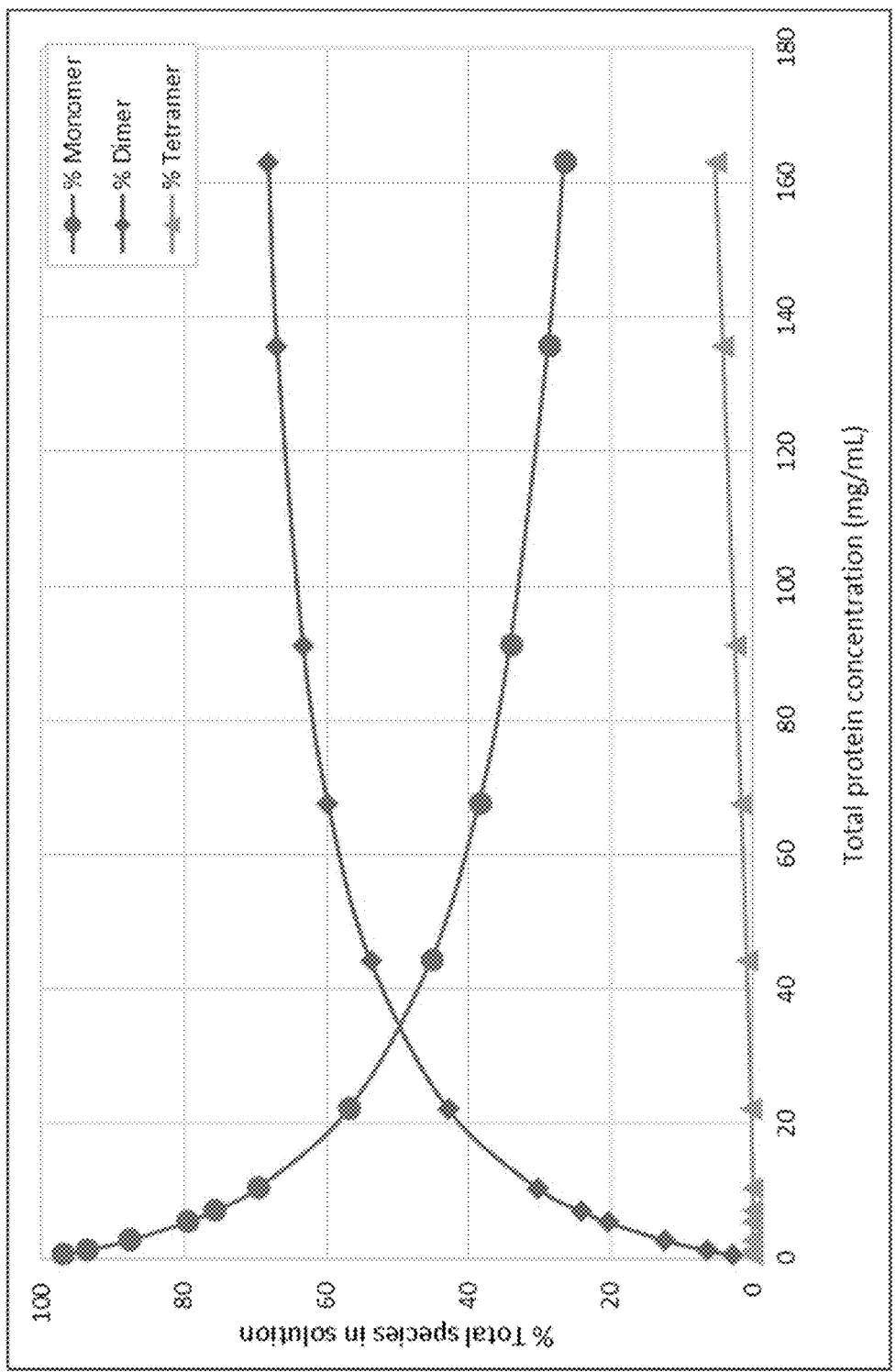
FIG. 5 is a graph showing Total KPL-404 species Population by CG-MALS for formulation B.

Similarly, no reversible associations could be modeled with the highest concentration points included. Due to strong repulsive interactions masking underlying attractive interactions, the highest concentration that could be fit with the reversible associations model was ~163 mg/mL with reversible dimer and hexamer (FIG. 5).

Figure 6:
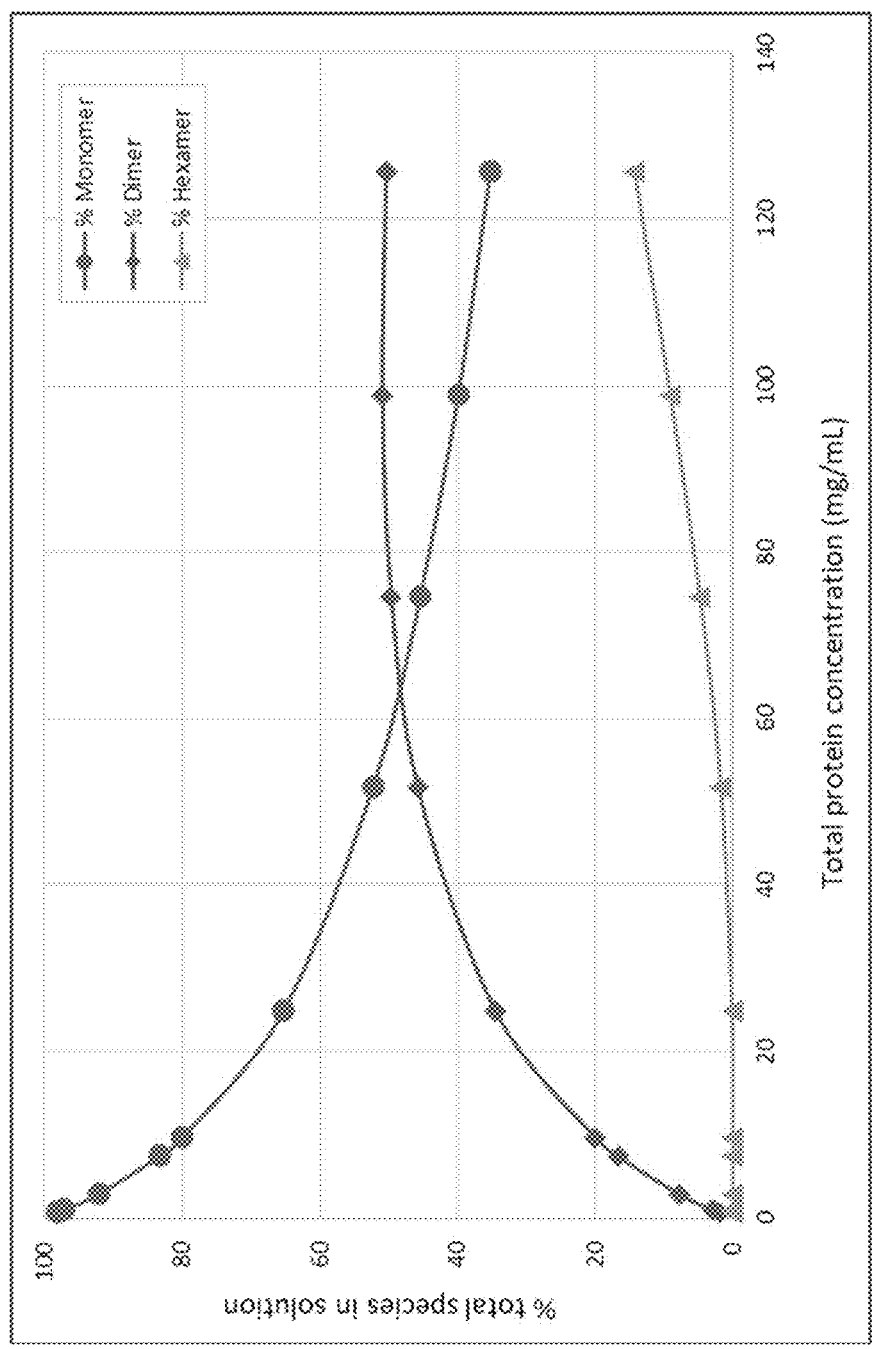
FIG. 6 is a graph showing Total KPL-404 species Population by CG-MALS for formulation C.

The percentage of reversible oligomers exceed the monomer at ~35 mg/mL. Reversible dimer was present even at the lowest concentration (~0.5 mg/mL), CG-MALS Results for Formulation C Similarly, no reversible associations could be modeled with the highest concentration points included. Due to strong repulsive interactions masking underlying attractive interactions, the highest concentration we could fit with the reversible associations model was ~126 mg/mL with reversible dimer and hexamer (FIG. 6).

The percentage of reversible oligomers exceed the monomer at ~60 mg/mL. Reversible hexamer starts to form at ~25 mg/mL. Approximately 2% dimer was present even at lowest total protein concentration In summary, CG-MALS demonstrates KPL-404 readily forms reversible dimers and higher ordered oligomer that are not detected by SEC (which dilutes to ~1 mg/mL prior to injection).

Results were generally consistent with a hard sphere repulsive behavior, with underlying attractive behavior in all formulations as indicated by the need to include reversible associations in global analysis.

Formulation A was more effective at inhibiting formation of reversible oligomers below 125 mg/mL, but data were not fittable at higher concentrations.

Formulation B was the least stable with respect to oligomerization, with reversible oligomers becoming the dominant species at ~35 mg/mL.

Formulation C shows oligomers become the dominant species at >60 mg/mL, and has lower viscosity compared to formulation A, which is consistent with lower energy self-association at elevated concentrations for Formulation C.

These data suggest that KPL-404 is less prone to aggregation not only at concentrations exceeding 200 mg/mL, but also at lower concentrations, e.g., 150-200 mg/mL. Both the rheology and light scattering data suggest that KPL-404 self-association tends to increase with increasing concentration. The shear-thinning data reveal a notable and unexpected difference between the self-association dynamics of formulation C from the other formulations, suggesting that arginine and glutamate affect these interactions via a different mechanism. The light scattering data demonstrate that KPL-404 is predominantly a monomer in Formulations A, B and C below ~100 mg/mL. At higher concentrations, however, these data suggest that Formulation C has a superior ratio of reversible dimer to non-reversible dimer compared to Formulations A and B.

Syringeability Characterization.

Figure 7:
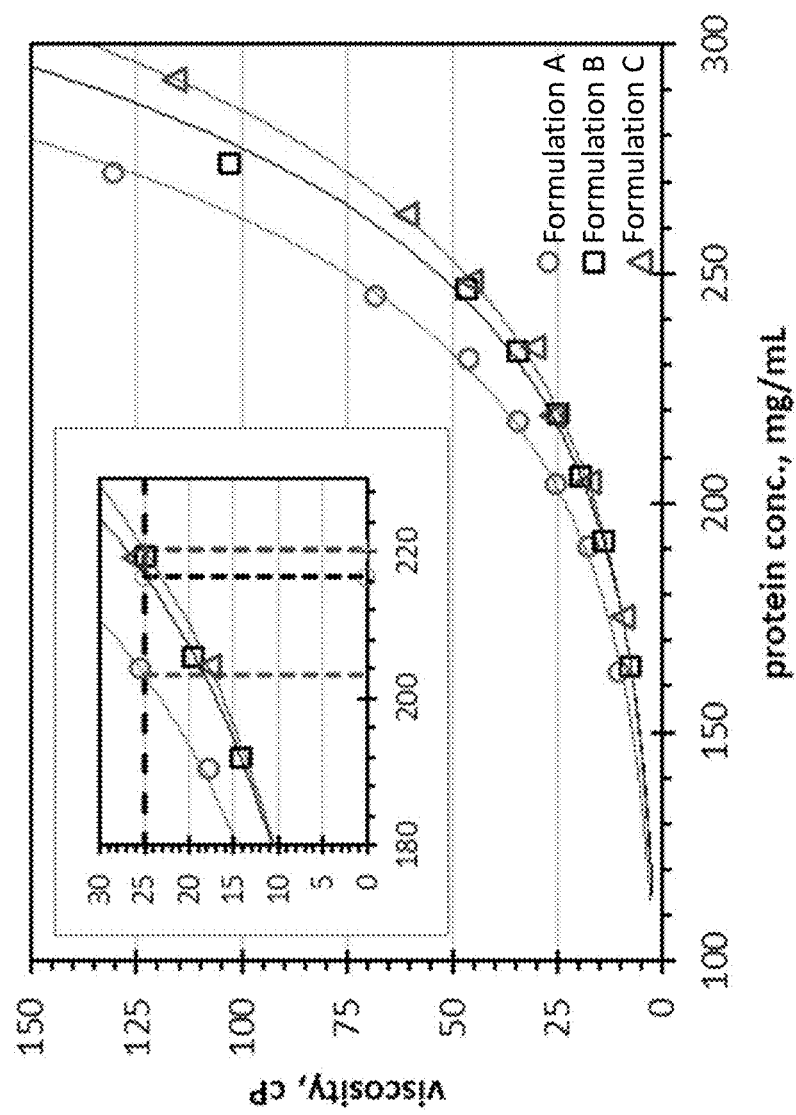
FIG. 7 is a graph showing Exponential dependence of measured viscosity vs protein concentration for formulation A (circles), B (squares), and C (triangles).
Figure 8:
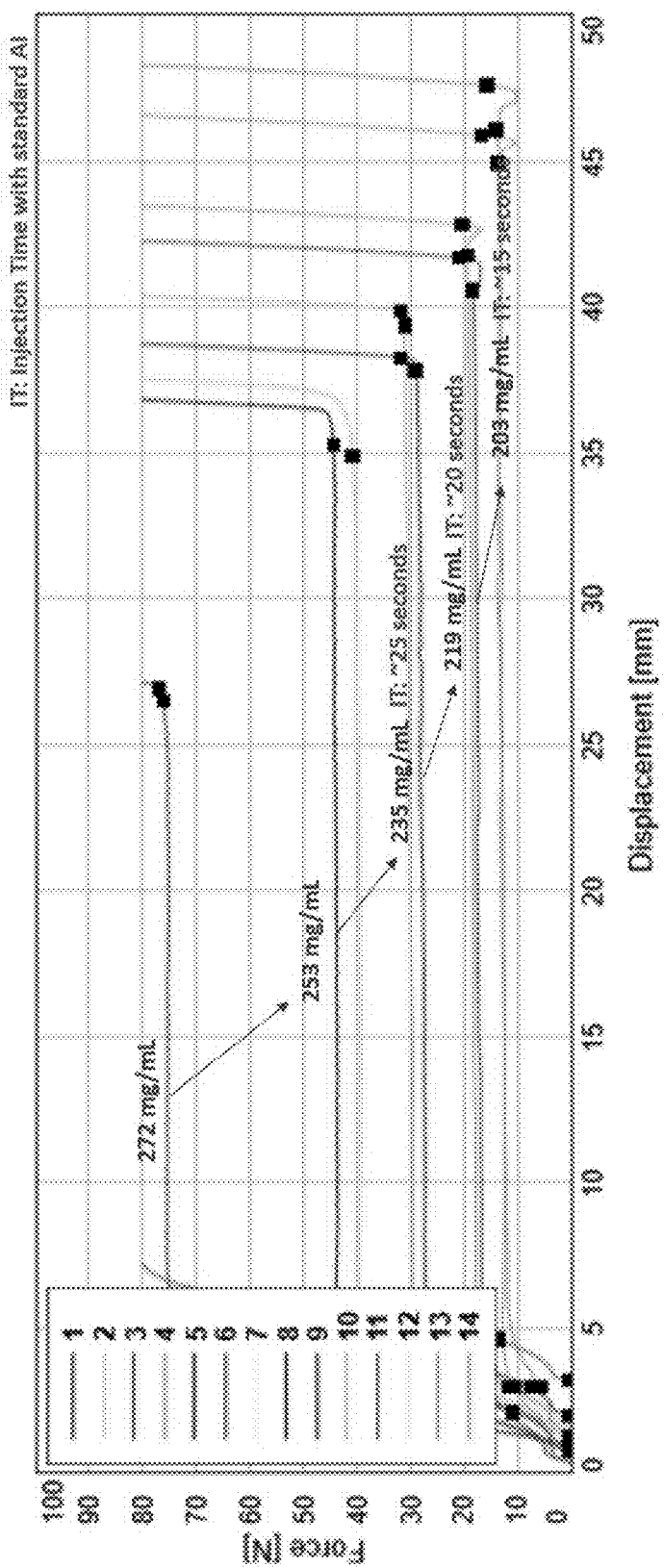
FIG. 8 is a graph showing Instron Force Profiles, KPL-404 in Formulation A, with Injection times from a Standard Ypsomate Autoinjector (2.25 mL).
Figure 9:
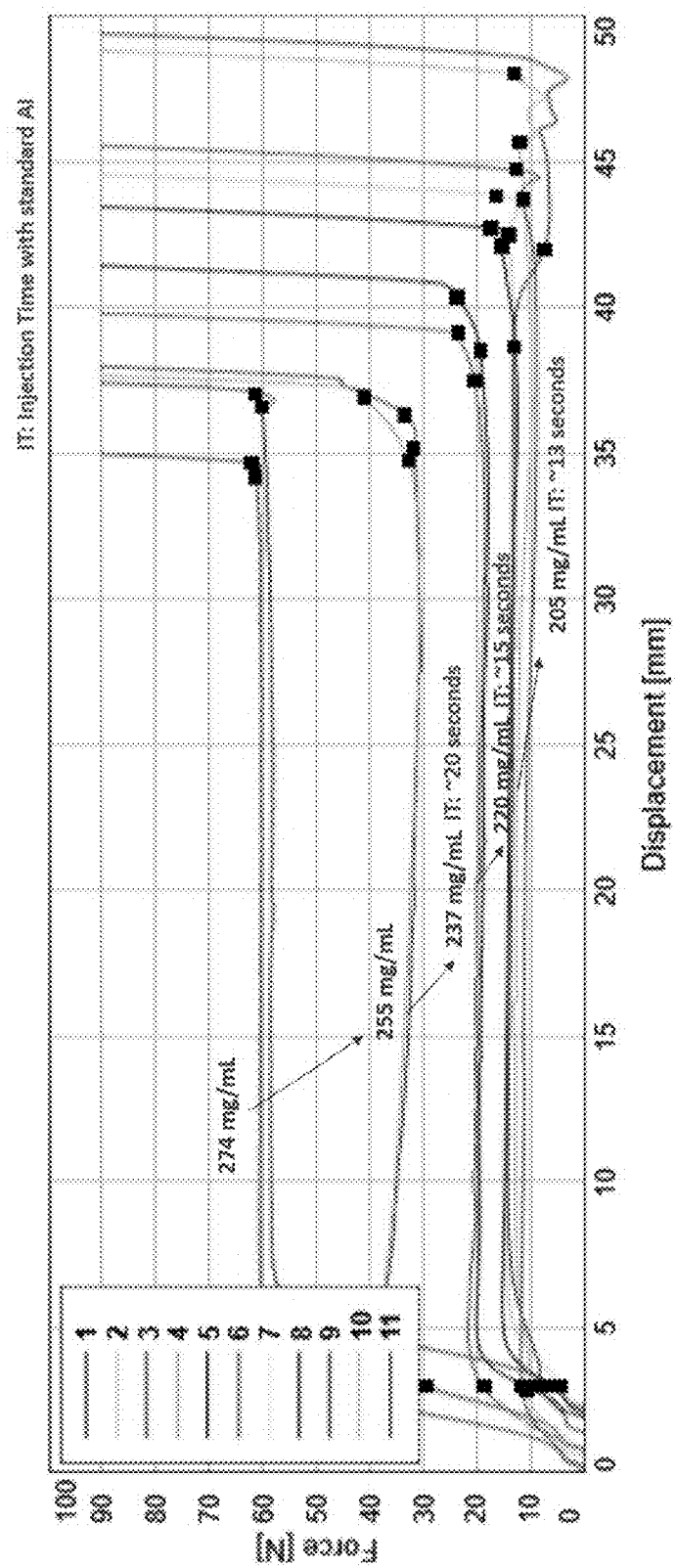
FIG. 9 is a graph showing Instron Force Profiles, KPL-404 in Formulation B, with Injection times from a Standard Ypsomate Autoinjector (2.25 mL).
Figure 10A:
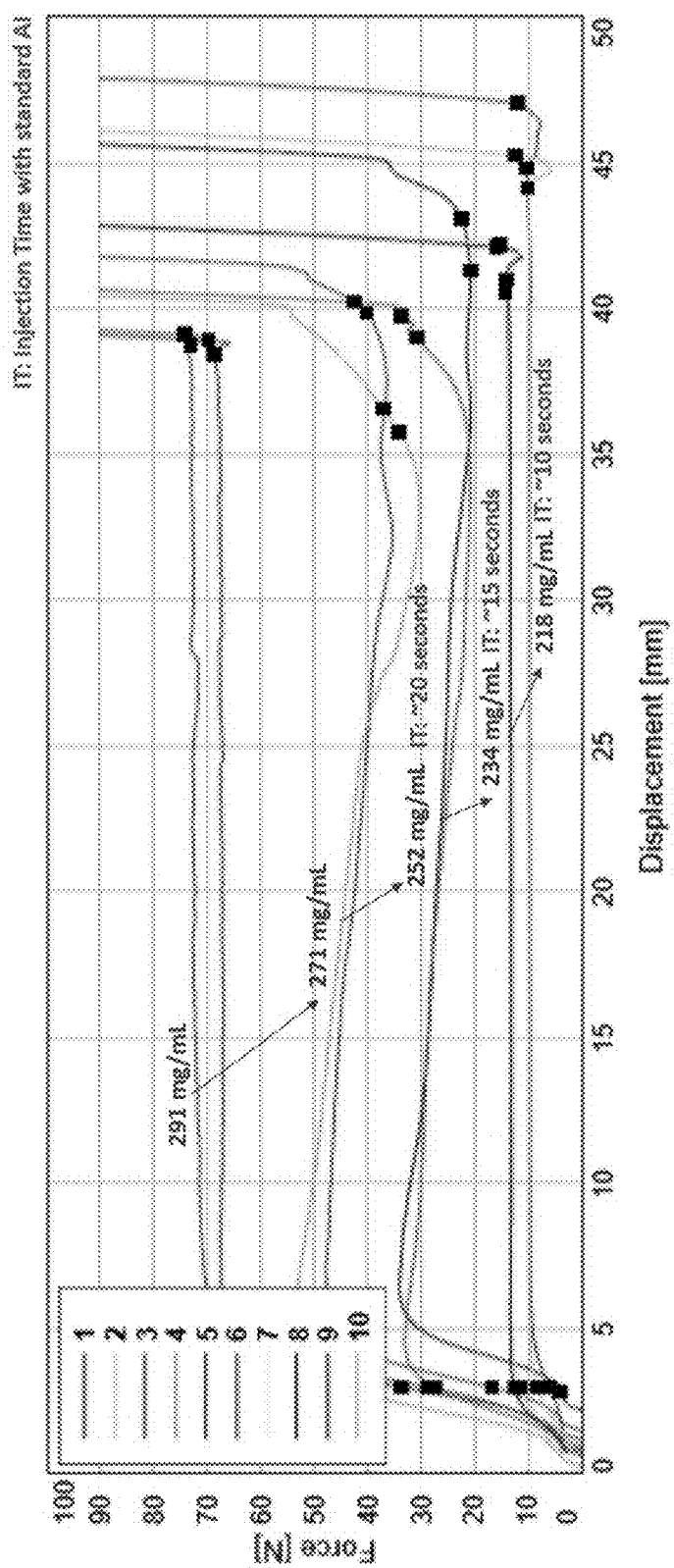
FIGS. 10A and 10B are graphs showing Instron Force Profiles, KPL-404 in Formulation C, with Injection times from a Standard Ypsomate (FIG. 10A) or Ypsomate Pro (FIG. 10B) Autoinjector (2.25 mL).
Figure 10B:
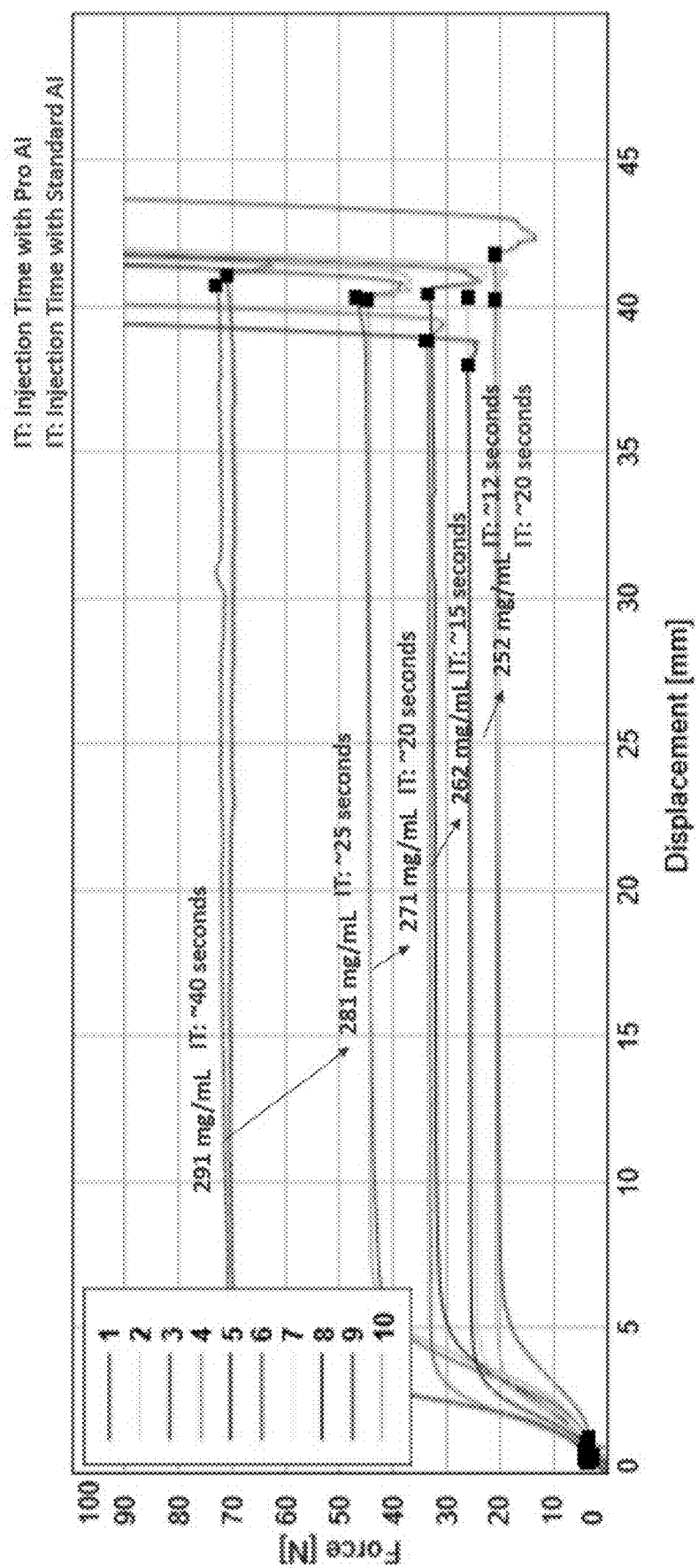

Viscosity was assessed as a function of variable concentration for each of the three formulations, Table 4 and FIG. 7.

Viscosity varied exponentially with respect to protein concentration. The inset in FIG. 7 highlights the KPL-404 concentration where a given formulation crosses 25 cP, a theoretical upper limit on syringeability based on extrusion force. Formulation A with sucrose exceeded 25 cP at ~200 mg/mL, Formulations B and C exceeded 25 cP above 220 mg/mL, with Formulation C being slightly less viscous than B.

TABLE 4

Conditions for KPL-404 Current Formulation PFS Stability Study.

| Dilution Factor | KPL-404-A nominal conc, mg/mL | Viscosity of A, cP | KPL-404-B nominal conc, mg/mL | Viscosity of B, cP | KPL-404-C nominal conc, mg/mL | Viscosity of C, cP |
|---|---|---|---|---|---|---|
| 1.00 | 272.0 | 130.8 | 274.0 | 103.0 | 292.0 | 116.0 |
| 0.90 | 244.8 | 68.4 | 246.6 | 46.4 | 262.8 | 61.2 |
| 0.85 | 231.2 | 46.1 | 232.9 | 34.5 | 248.2 | 45.6 |
| 0.80 | 217.6 | 34.7 | 219.2 | 24.8 | 233.6 | 31.0 |
| 0.75 | 204.0 | 25.5 | 205.5 | 19.6 | 219.0 | 26.1 |
| 0.70 | 190.4 | 17.8 | 191.8 | 14.2 | 204.4 | 17.9 |
| 0.60 | 163.2 | 10.3 | 164.4 | 8.0 | 175.2 | 9.4 |

Each of Formulations A, B, and C were filled by hand into a 2.25 mL BD Neopak syringe. The same sample was tested five times with a new syringe for each test. Instron testing was performed, recording gliding forces as a function of protein concentration for each formulation, Table 5. To reserve sample, testing utilized the highest concentration sample of each formulation, diluting the recovered sample with buffer to generate lower concentration. The results show decreasing injection force as a function of decreasing concentration.

Injection times for the lowest three concentrations were recorded using manually assembled Auto-Injectors (AI) with each of the candidate formulations in a 2.25 mL BD Neopak syringe, Table 5. The time was established by video recording, calculating time from frame rate and the number of frames from first to last drop.

The Standard Ypsomate AI was Tested in all Three Candidates:

Injection times (into air) for formulation A were ≥20 s at 220 mg/mL and higher and was ~15 s at 200 mg/mL.

Injection times for formulation B were ≥20 s at 237 mg/mL and were 15 s at 220 mg/mL.

Injection times for formulation C were ≥20 s at 252 mg/mL and were 15 s at 234 mg/mL.

The Ypsomate Pro AI was Tested Only on Formulation C:

Injection times for formulation C were ≥20 s at 271 mg/mL and were 15 s at 262 mg/mL.

See Table 5 and FIGS. 8-10B.

TABLE 5

Syringeability of KPL-404 High Concentration Formulation Candidates.

| Formulation | Concentration, mg/mL | End of Injection Gliding Force, N | Injection Time for Std Yposmate Al, s | Injection Time for Yposmate-Pro Al, s |
|---|---|---|---|---|
| A | 272 | ~80 | N.A. | N.A. |
|   | 253 | ~45 | N.A. | N.A. |
|   | 235 | ~30 | ~25 | N.A. |
|   | 219 | ~20 | ~20 | N.A. |
|   | 203 | ~15 | ~15 | N.A. |
| B | 274 | ~60 | N.A. | N.A. |
|   | 255 | ~30 | N.A. | N.A. |
|   | 237 | ~20 | ~20 | N.A. |
|   | 220 | ~15 | ~15 | N.A. |
|   | 205 | ~10 | ~10 | N.A. |
| C | 291 | ~70 | N.A. | ~40 |
|   | 281 | ~45 | N.A. | ~25 |
|   | 271 | ~33 | N.A. | ~20 |
|   | 262 | ~26 | N.A. | ~15 |
|   | 252 | ~20 | ~20 | ~12 |
|   | 234 | ~15 | ~15 | N.A. |
|   | 218 | ~10 | ~10 | N.A. |

In summary, glide forces and injection times generally correlate with viscosities, but Formulation C consistently achieved higher concentrations as compared to Formulation B, with the sucrose Formulation A performing poorer than B and C.

Stability of 200 mg/mL and >200 mg/mL KPL-404 Formulations

All three formulations were examined for stability at 200 mg/mL, which is the upper concentration limit for Formulation A based on injectability data.

Injectability data suggests that Formulation B can support 220 mg/mL. For head-to-head comparison, both Formulations A and B were put on short-term stability (3 months) at 220 mg/mL. Injectability data suggests Formulation C can support 235 mg/mL, which was likewise put on short-term stability (3 mo). The data are summarized in Tables 6-14.

TABLE 6

Formulation A, 200 mg/mL stability, 5° C.

| Tests | Criteria | t0 | 2 w, 5 C. | 1 M, 5 C. | 2 M, 5 C. | 3 M, 5 C. | 6 M, 5 C. | 9 M, 5 C. | 12 M, 5 C. |
|---|---|---|---|---|---|---|---|---|---|
| icIEF-% Acidic | Report Result | 33.4 | NT | NT | NT | 34.8 | NT | NT | NT |
| icIEF-% Main | Report Result | 50.2 | NT | NT | NT | 47.9 | NT | NT | NT |
| icIEF-% Basic | Report Result | 16.4 | NT | NT | NT | 17.3 | NT | NT | NT |
| NR CE-SDS-% IgG | Report Result | NT | NT | NT | NT | 99.0 | NT | NT | NT |
| NR CE-SDS-% Highest Impurity | Report Result | NT | NT | NT | NT | 0.5 | NT | NT | NT |
| SEC % Main | ≥95% | 98.9 | 98.6 | 98.7 | 98.5 | 98.5 | 98.2 | 98.2 | 98.1 |
| SEC % HMW | Report Result | 1.1 | 1.4 | 1.4 | 1.5 | 1.5 | 1.8 | 1.9 | 1.9 |
| SEC % LMW | Report Result | ND | ND | ND | ND | ND | ND | ND | ND |
| SVP analysis |  |  |  |  |  |  |  |  |  |
| ≥2 to <10 μm | Report Result | 31 | 21640 | 1965 | 2455 | 7485 | 6080 | 3975 | 26117 |
| ≥10 μm | Report Result | 1 | 440 | 55 | 90 | 195 | 160 | 175 | 95 |
| ≥25 μm | Report Result | 99 | 10 | 0 | 25 | 15 | 40 | 25 | 0 |

NT = Not tested,
ND = Not detectable (<LOD)

TABLE 7

Formulation A, 200 mg/mL stability: agitation, stressed at 40° C., accelerated at 25° C.

| Tests | Criteria | t0 | 1 w, agitation | 1 w, 40 C. | 2 w, 40 C. | 1 M, 40 C. | 1 w, 25 C. | 2 w, 25 C. | 1 M, 25 C. | 2 M, 25 C. | 3 M, 25 C. | 6 M, 25 C. |
|---|---|---|---|---|---|---|---|---|---|---|---|---|
| icIEF-% Acidic | Report Result | 33.4 | NT | NT | NT | 44.4 | NT | NT | NT | NT | 39.5 | NT |
| icIEF-% Main | Report Result | 50.2 | NT | NT | NT | 40.2 | NT | NT | NT | NT | 44.3 | NT |

TABLE 7-continued

Formulation A, 200 mg/mL stability: agitation, stressed at 40° C., accelerated at 25° C.

| Tests | Criteria | t0 | 1 w, agitation | 1 w, 40 C. | 2 w, 40 C. | 1 M, 40 C. | 1 w, 25 C. | 2 w, 25 C. | 1 M, 25 C. | 2 M, 25 C. | 3 M, 25 C. | 6 M, 25 C. |
|---|---|---|---|---|---|---|---|---|---|---|---|---|
| icIEF-% Basic | Report Result | 16.4 | NT | NT | NT | NT | 15.3 | NT | NT | NT | 16.2 | NT |
| NR CE-SDS-% IgG | Report Result | NT | NT | NT | NT | NT | 97.8 | NT | NT | NT | 98.4 | NT |
| NR CE-SDS-% Highest Impurity | Report Result | NT | NT | NT | NT | NT | 0.7 | NT | NT | NT | 0.6 | NT |
| SEC % Main | ≥95% | 98.9 | 98.7 | 97.7 | 97.3 | 96.2 | 98.5 | 98.3 | 98.2 | 97.8 | 97.6 | 97.1 |
| SEC % HMW | Report Result | 1.1 | 1.3 | 2.3 | 2.7 | 3.7 | 1.6 | 1.7 | 1.8 | 2.2 | 2.4 | 3.0 |
| SEC % LMW | Report Result | ND | ND | 0.0 | 0.0 | 0.1 | ND | ND | ND | 0.0 | 0.1 | ND |
| SVP analysis | | | | | | | | | | | | |
| ≥2 to <10 μm | Report Result | 31 | 0 | 24270 | 4800 | 1685 | 5710 | 12060 | 1595 | 2100 | 11995 | |
| ≥10 μm | Report Result | 1 | 1 | 310 | 120 | 15 | 140 | 330 | 25 | 30 | 215 | |
| ≥25 μm | Report Result | 99 | 99 | 40 | 20 | 0 | 20 | 30 | 5 | 5 | 40 | |

NT = Not tested,
ND = Not detectable (<LOD)

TABLE 8

Formulation A, 200 mg/mL stability, frozen at −20° C. or −70° C.

| Tests | Criteria | $t_0$ | 3 M, −20 C. | 3 M, −70 C. | 6 M, −70 C. | 9 M, −70 C. | 12 M, −70 C. |
|---|---|---|---|---|---|---|---|
| icIEF-% Acidic | Report Result | 33.4 | NT | NT | NT | 36.0 | 34.9 |
| icIEF-% Main | Report Result | 50.2 | NT | NT | NT | 47.1 | 48.2 |
| icIEF-% Basic | Report Result | 16.4 | NT | NT | NT | 16.9 | 16.9 |
| NR CE-SDS-% IgG | Report Result | NT | NT | NT | NT | 99.0 | 98.9 |
| NR CE-SDS-% Highest Impurity | Report Result | NT | NT | NT | NT | 0.5 | 0.5 |
| SEC % Main | ≥95% | 98.9 | 98.7 | 98.7 | NT | 98.8 | 98.8 |
| SEC % HMW | Report Result | 1.1 | 1.4 | 1.3 | NT | 1.2 | 1.2 |
| SEC % LMW | Report Result | ND | ND | ND | NT | ND | ND |
| SVP analysis | | | | | | | |
| ≥2 to <10 μm | Report Result | 31 | 44720 | 54875 | NT | 178840 | 126116 |
| ≥10 μm | Report Result | 1 | 2310 | 3085 | NT | 3700 | 3725 |
| ≥25 μm | Report Result | 99 | 350 | 450 | NT | 307 | 317 |

NT = Not tested,
ND = Not detectable (<LOD)

TABLE 9

Formulation B, 200 mg/mL stability, 5° C.

| Tests | Criteria | $t_0$ | 2 w, 5 C. | 1 M, 5 C. | 2 M, 5 C. | 3 M, 5 C. | 6 M, 5 C. | 9 M, 5 C. | 12 M, 5 C. |
|---|---|---|---|---|---|---|---|---|---|
| icIEF-% Acidic | Report Result | 34.6 | NT | NT | NT | 34.7 | NT | NT | NT |
| icIEF-% Main | Report Result | 50.9 | NT | NT | NT | 48.3 | NT | NT | NT |
| icIEF-% Basic | Report Result | 14.5 | NT | NT | NT | 17.0 | NT | NT | NT |

TABLE 9-continued

Formulation B, 200 mg/mL stability, 5° C.

| Tests | Criteria | $t_0$ | 2 w, 5 C. | 1 M, 5 C. | 2 M, 5 C. | 3 M, 5 C. | 6 M, 5 C. | 9 M, 5 C. | 12 M, 5 C. |
|---|---|---|---|---|---|---|---|---|---|
| NR CE-SDS-% IgG | Report Result | NT | NT | NT | NT | 99.1 | NT | NT | NT |
| NR CE-SDS-% Highest Impurity | Report Result | NT | NT | NT | NT | 0.4 | NT | NT | NT |
| SEC % Main | ≥95% | 98.9 | 98.7 | 98.6 | 98.5 | 98.5 | 98.2 | 98.2 | 98.1 |
| SEC % HMW | Report Result | 1.1 | 1.3 | 1.4 | 1.5 | 1.5 | 1.8 | 1.9 | 1.9 |
| SEC % LMW | Report Result | ND | ND | ND | ND | ND | ND | ND | ND |
| SVP analysis | | | | | | | | | |
| ≥2 to <10 μm | Report Result | 0 | 4980 | 2665 | 1270 | 6570 | 14130 | 5835 | 9111 |
| ≥10 μm | Report Result | 1 | 40 | 110 | 40 | 160 | 345 | 165 | 275 |
| ≥25 μm | Report Result | 99 | 20 | 5 | 15 | 35 | 15 | 5 | 0 |

NT = Not tested,
ND = Not detectable (<LOD)

TABLE 10

Formulation B, 200 mg/mL stability: agitation, stressed at 40° C., accelerated at 25° C.

| Tests | Criteria | $t_0$ | agitation | 1 w, 40 C. | 2 w, 40 C. | 1 M, 40 C. | 1 w, 25 C. | 2 w, 25 C. | 1 M, 25 C. | 2 M, 25 C. | 3 M, 25 C. | 6 M, 25 C. |
|---|---|---|---|---|---|---|---|---|---|---|---|---|
| icIEF-% Acidic | Report Result | 34.6 | NT | NT | NT | NT | 44.2 | NT | NT | NT | 38.7 | NT |
| icIEF-% Main | Report Result | 50.9 | NT | NT | NT | NT | 39.9 | NT | NT | NT | 44.6 | NT |
| icIEF-% Basic | Report Result | 14.5 | NT | NT | NT | NT | 15.9 | NT | NT | NT | 16.8 | NT |
| NR CE-SDS-% IgG | Report Result | NT | NT | NT | NT | NT | 97.9 | NT | NT | NT | 98.5 | NT |
| NR CE-SDS-% Highest Impurity | Report Result | NT | NT | NT | NT | NT | 0.6 | NT | NT | NT | 0.6 | NT |
| SEC % Main | ≥95% | 98.9 | 98.5 | 97.6 | 97.2 | 96.1 | 98.4 | 98.4 | 98.1 | 97.9 | 97.6 | 97.1 |
| SEC % HMW | Report Result | 1.1 | 1.5 | 2.4 | 2.8 | 3.8 | 1.6 | 1.6 | 1.9 | 2.1 | 2.4 | 2.9 |
| SEC % LMW | Report Result | ND | ND | 0.1 | 0.1 | 0.1 | ND | ND | ND | ND | 0.0 | ND |
| SVP analysis | | | | | | | | | | | | |
| ≥2 to <10 μm | Report Result | 0 | 0 | 8510 | 5990 | 1950 | 5440 | 6080 | 2365 | 1695 | 9045 | NT |
| ≥10 μm | Report Result | 1 | 2 | 170 | 190 | 35 | 210 | 110 | 100 | 30 | 385 | NT |
| ≥25 μm | Report Result | 99 | 99 | 40 | 30 | 5 | 40 | 0 | 10 | 10 | 70 | NT |

NT = Not tested,
ND = Not detectable (<LOD)

TABLE 11

Formulation B, 200 mg/mL stability, frozen at −20° C. or −70° C.

| Tests | Criteria | $t_0$ | 3 M, −20 C. | 3 M, −70 C. | 6 M, −70 C. | 9 M, −70 C. | 12 M, −70 C. |
|---|---|---|---|---|---|---|---|
| icIEF-% Acidic | Report Result | 34.6 | NT | NT | NT | 35.0 | 34.9 |
| icIEF-% Main | Report Result | 50.9 | NT | NT | NT | 48.2 | 48.6 |
| icIEF-% Basic | Report Result | 14.5 | NT | NT | NT | 16.7 | 16.5 |
| NR CE-SDS-% IgG | Report Result | NT | NT | NT | NT | 99.0 | 98.9 |

TABLE 11-continued

Formulation B, 200 mg/mL stability, frozen at −20° C. or −70° C.

| Tests | Criteria | t₀ | 3 M, −20 C. | 3 M, −70 C. | 6 M, −70 C. | 9 M, −70 C. | 12 M, −70 C. |
|---|---|---|---|---|---|---|---|
| NR CE-SDS-% Highest Impurity | Report Result | NT | NT | NT | NT | 0.5 | 0.5 |
| SEC % Main | ≥95% | 98.9 | 98.5 | 98.7 | NT | 98.8 | 98.7 |
| SEC % HMW | Report Result | 1.1 | 1.5 | 1.3 | NT | 1.2 | 1.3 |
| SEC % LMW | Report Result | ND | ND | ND | NT | ND | ND |
| SVP analysis | | | | | | | |
| ≥2 to <10 μm | Report Result | 0 | 27225 | 90130 | NT | 100040 | 169540 |
| ≥10 μm | Report Result | 1 | 1665 | 1870 | NT | 2640 | 2968 |
| ≥25 μm | Report Result | 99 | 105 | 145 | NT | 233 | 143 |

NT = Not tested,
ND = Not detectable (<LOD)

TABLE 12

Formulation C, 200 mg/mL stability, 5° C.

| Tests | Criteria | t₀ | 2 w, 5 C. | 1 M, 5 C. | 2 M, 5 C. | 3 M, 5 C. | 6 M, 5 C. | 9 M, 5 C. | 12 M, 5 C. |
|---|---|---|---|---|---|---|---|---|---|
| icIEF-% Acidic | Report Result | 31.9 | NT | NT | NT | 35.6 | NT | NT | NT |
| icIEF-% Main | Report Result | 54.6 | NT | NT | NT | 47.7 | NT | NT | NT |
| icIEF-% Basic | Report Result | 13.5 | NT | NT | NT | 16.7 | NT | NT | NT |
| NR CE-SDS-% IgG | Report Result | NT | NT | NT | NT | 99.1 | NT | NT | NT |
| NR CE-SDS-% Highest Impurity | Report Result | NT | NT | NT | NT | 0.5 | NT | NT | NT |
| SEC % Main | ≥95% | 99.1 | 98.9 | 98.8 | 98.8 | 98.7 | 98.7 | 98.7 | 98.6 |
| SEC % HMW | Report Result | 0.9 | 1.1 | 1.2 | 1.3 | 1.3 | 1.3 | 1.4 | 1.4 |
| SEC % LMW | Report Result | ND | ND | ND | ND | ND | ND | ND | ND |
| SVP analysis | | | | | | | | | |
| ≥2 to <10 μm | Report Result | 25 | 4250 | 2250 | 3570 | 10850 | 22315 | 13830 | 41865 |
| ≥10 μm | Report Result | 1 | 50 | 95 | 80 | 240 | 720 | 165 | 389 |
| ≥25 μm | Report Result | 99 | 0 | 5 | 5 | 5 | 5 | 10 | 0 |

NT = Not tested,
ND = Not detectable (<LOD)

TABLE 13

Formulation C, 200 mg/mL stability: agitation, stressed at 40° C., accelerated at 25° C.

| Tests | Criteria | t₀ | agitation | 1 w, 40 C. | 2 w, 40 C. | 1 M, 40 C. | 1 w, 25 C. | 2 w, 25 C. | 1 M, 25 C. | 2 M, 25 C. | 3 M, 25 C. | 6 M, 25 C. |
|---|---|---|---|---|---|---|---|---|---|---|---|---|
| icIEF-% Acidic | Report Result | 31.9 | NT | NT | NT | 45.7 | NT | NT | NT | NT | 39.1 | NT |
| icIEF-% Main | Report Result | 54.6 | NT | NT | NT | 39.4 | NT | NT | NT | NT | 44.5 | NT |
| icIEF-% Basic | Report Result | 13.5 | NT | NT | NT | 15.0 | NT | NT | NT | NT | 16.4 | NT |
| NR CE-SDS-% IgG | Report Result | NT | NT | NT | NT | 97.5 | NT | NT | NT | NT | 98.4 | NT |
| NR CE-SDS-% Highest Impurity | Report Result | NT | NT | NT | NT | 0.8 | NT | NT | NT | NT | 0.6 | NT |

TABLE 13-continued

Formulation C, 200 mg/mL stability: agitation, stressed at 40° C., accelerated at 25° C.

| Tests | Criteria | $t_0$ | agitation | 1 w, 40 C. | 2 w, 40 C. | 1 M, 40 C. | 1 w, 25 C. | 2 w, 25 C. | 1 M, 25 C. | 2 M, 25 C. | 3 M, 25 C. | 6 M, 25 C. |
|---|---|---|---|---|---|---|---|---|---|---|---|---|
| SEC % Main | ≥95% | 99.1 | 98.8 | 98.1 | 97.8 | 97.0 | 98.7 | 98.8 | 98.6 | 98.3 | 98.2 | 97.8 |
| SEC % HMW | Report Result | 0.9 | 1.2 | 1.8 | 2.1 | 2.9 | 1.3 | 1.2 | 1.5 | 1.7 | 1.8 | 2.2 |
| SEC % LMW | Report Result | ND | ND | 0.1 | 0.0 | 0.1 | ND | ND | ND | 0.0 | 0.0 | 0.1 |
| SVP analysis | | | | | | | | | | | | |
| ≥2 to <10 μm | Report Result | 25 | 0 | 4980 | 7410 | 4005 | 4026 | 3760 | 6067 | 4565 | 12795 | NT |
| ≥10 μm | Report Result | 1 | 1 | 120 | 260 | 60 | 67 | 160 | 180 | 145 | 210 | NT |
| ≥25 μm | Report Result | 99 | 99 | 40 | 30 | 0 | 40 | 40 | 20 | 15 | 10 | NT |

NT = Not tested,
ND = Not detectable (<LOD)

TABLE 14

Formulation C, 200 mg/mL stability, frozen at −20° C. or −70°C.

| Tests | Criteria | $t_0$ | 3 M, −20 C. | 3 M, −70 C. | 6 M, −70 C. | 9 M, −70 C. | 12 M, −70 C. |
|---|---|---|---|---|---|---|---|
| icIEF-% Acidic | Report Result | 31.9 | NT | NT | NT | 35.7 | 34.5 |
| icIEF-% Main | Report Result | 54.6 | NT | NT | NT | 47.2 | 48.6 |
| icIEF-% Basic | Report Result | 13.5 | NT | NT | NT | 17.1 | 16.9 |
| NR CE-SDS-% IgG | Report Result | NT | NT | NT | NT | 98.9 | 98.9 |
| NR CE-SDS-% Highest Impurity | Report Result | NT | NT | NT | NT | 0.6 | 0.6 |
| SEC % Main | ≥95% | 99.1 | 98.8 | 98.9 | NT | 99.0 | 99.0 |
| SEC % HMW | Report Result | 0.9 | 1.2 | 1.1 | NT | 1.0 | 1.0 |
| SEC % LMW | Report Result | ND | ND | ND | NT | ND | ND |
| SVP analysis | | | | | | | |
| ≥2 to <10 μm | Report Result | 25 | 36415 | 15600 | NT | 150695 | 88307 |
| ≥10 μm | Report Result | 1 | 1165 | 500 | NT | 3490 | 1026 |
| ≥25 μm | Report Result | 99 | 100 | 35 | NT | 210 | 32 |

NT = Not tested,
ND = Not detectable (<LOD)

Subsequent aggregation data were produced for Formulation A (100 mg/mL KPL-404 in 50 mM sodium acetate, 7% (w/v) sucrose, 0.01% (w/v) polysorbate 20, pH 5.4) KPL-404 up to 24 months at 2-8° C. In a first lot, the main peak in the SEC was 98.3% at T=0 and 97.6% at T=12 months and T=24 months, indicating a ΔSEC (main peak) of −0.71%, which was unchanged from 12 to 24 months. The high molecular weight (HMW) peak for the SEC, which represents aggregates of the antibody, was 1.3% at T=0, 1.6% at T=12 months, and 1.8% at T=24 months, indicating very little increase in aggregation over time. In a second lot, the main peak in the SEC was 98.6% at T=0 and 97.8% at T=12 months, indicating a ΔSEC (main peak) of −0.81%. Data were not produced to 24 months. The high molecular weight (HMW) peak for the SEC in the second lot was 0.9% at T=0, 1.4% at T=12 months, and 1.5% at T=18 months, also indicating very little increase in aggregation over time.

Aggregation data were also produced for Formulation C (200 mg/mL KPL-404 in 50 mM sodium acetate, 100 mM L-Arginine, 100 mM L-Glutamate, 0.02% polysorbate 20, pH 5.4) KPL-404 up to 12 months at 2-8° C. In a first lot, the protein exhibited an SEC main peak of 99.2% and 98.9% at T=0 and T=12 months, respectively, indicating a ΔSEC (main peak) of −0.3%. The HMW peak was 0.60% at T=0 and 0.70% at T=12 months, indicating a slight increase in aggregation over time. In a second lot, the protein exhibited an SEC main peak of 98.7% and 98.1% at T=0 and T=9 months, respectively, indicating a ΔSEC (main peak) of −0.61%. The HMW peak was 0.40% at T=0 and 0.70% at T=9 months, indicating a slight increase in aggregation over time.

Figure 11:
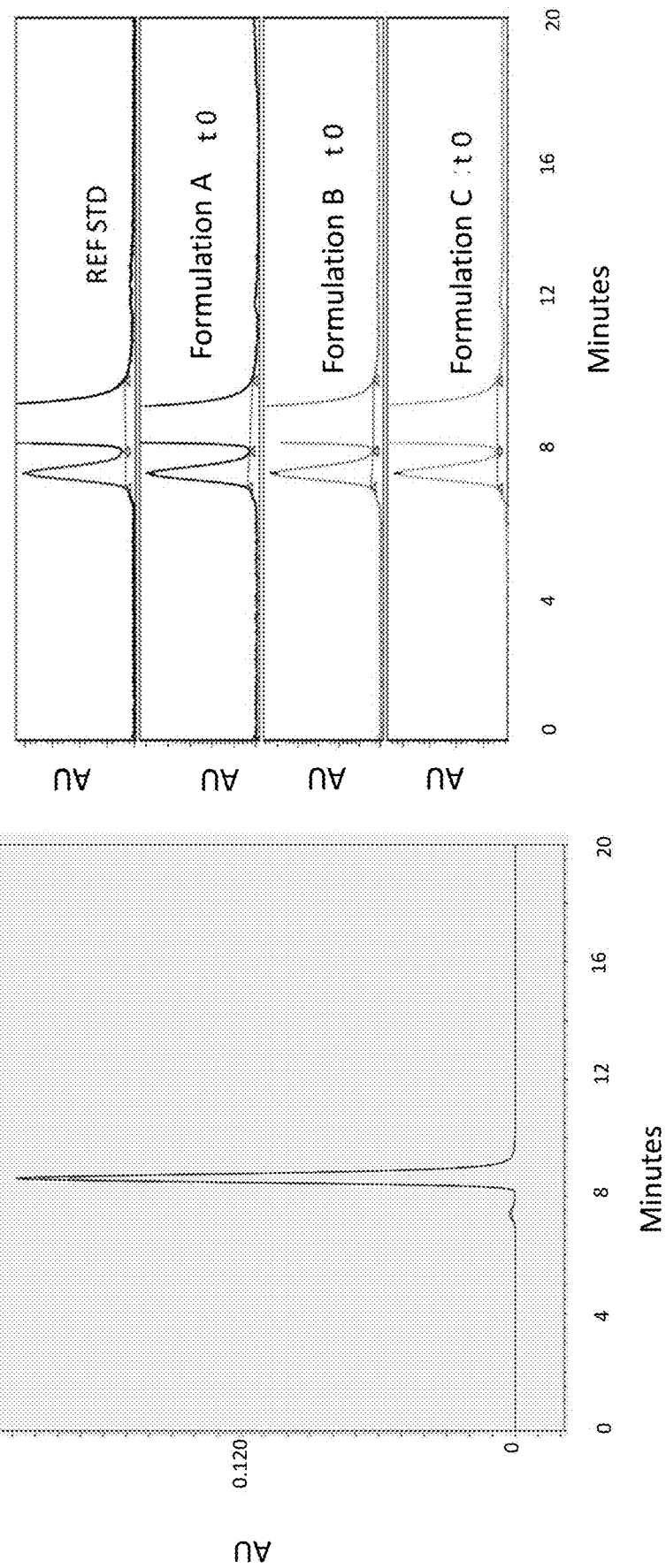
FIG. 11 is a set of SEC Chromatograms of Formulations A, B, and C, t=0 (initial). The right side shows an enhanced view of the left panel.

Aggregation by SEC is a major degradation pathway. FIG. 1 shows a set of graphs showing SEC results presented graphically for % Main, % HMW and % LMW species of KPL-404 for Formulations A, 1 and 2. Chromatograms of initial samples are shown in FIG. 11, showing initially all three formulations are essentially the same as the reference standard.

Figure 12:
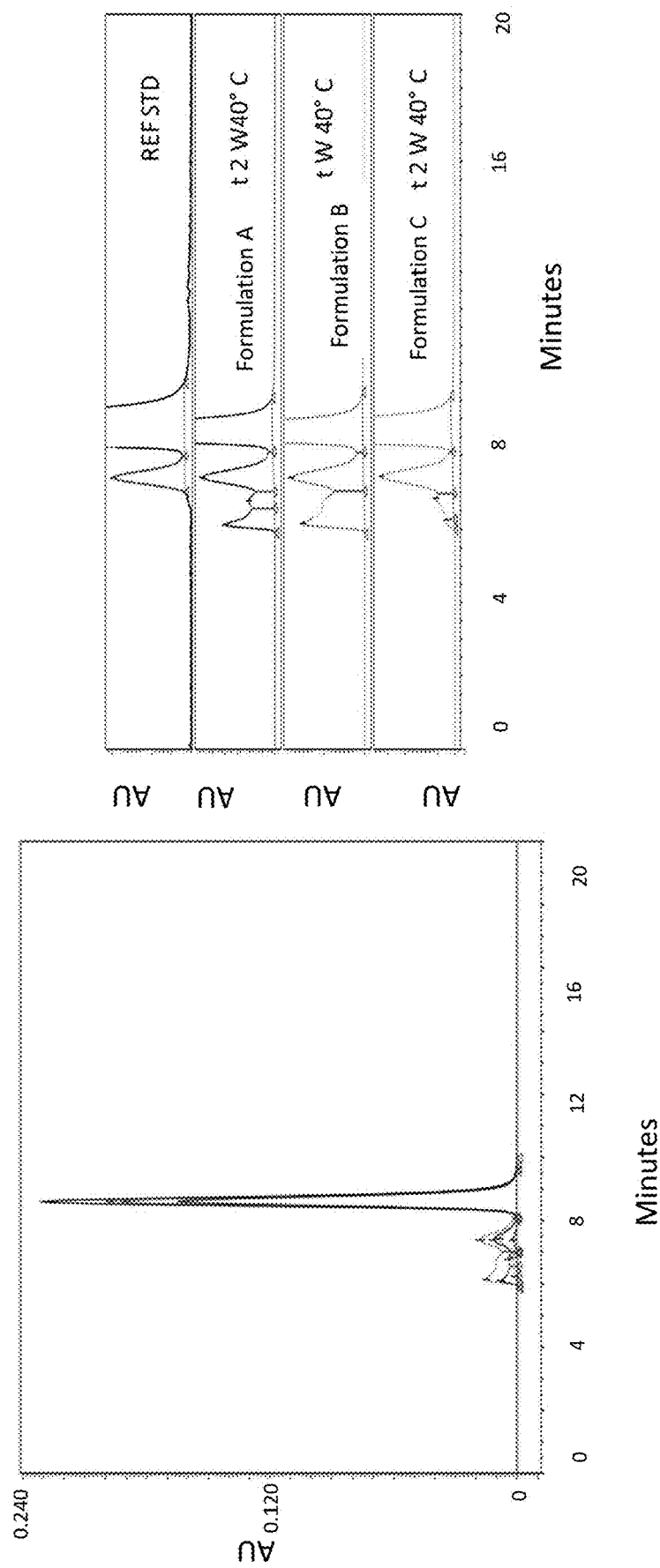
FIG. 12 is a set of SEC Chromatograms of Formulations A, B, and C, t=2w, 40° C. The right side shows an enhanced view of the left panel.

Following thermal stress at 40° C. for 2 weeks, FIG. 12, aggregation was observed for all three formulations, with species larger than a dimer formed for Formulations A and B. Formulation C minimized formation of higher-ordered species in comparison, consistent with the Arg/Glu excipients enabling higher protein concentrations of KPL-404 relative to sucrose and sorbitol.

Figure 13:
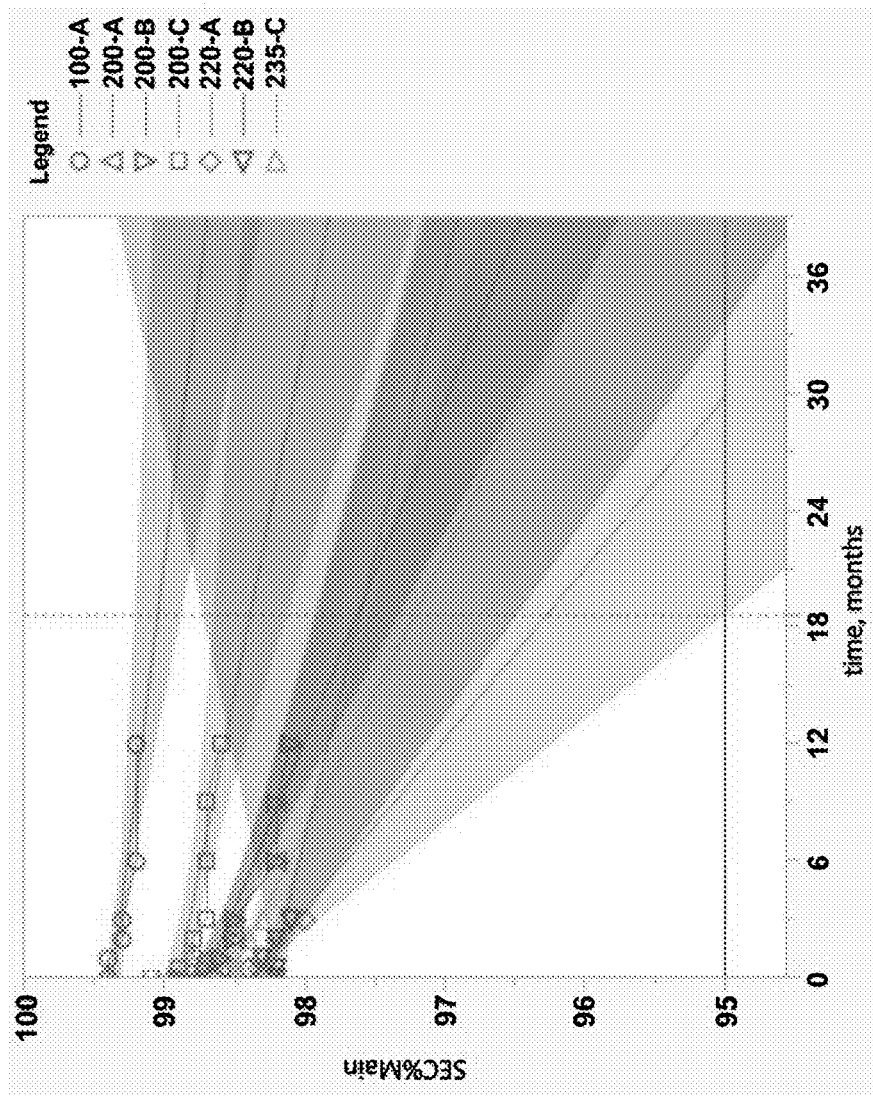
FIG. 13 is a graph showing SEC % Main as a function of time, 5° C. storage.
Figure 14:
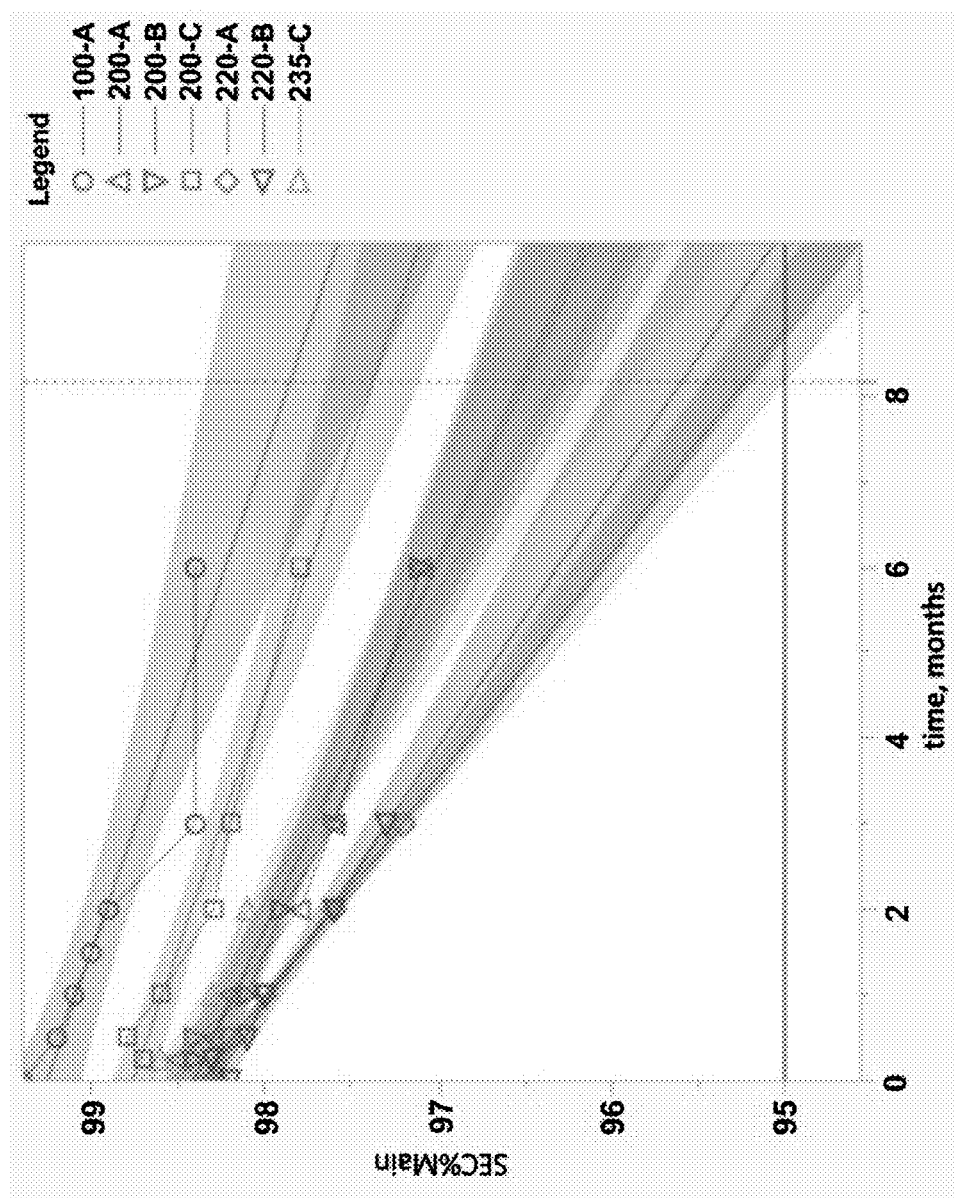
FIG. 14 is a graph showing SEC % Main as a function of time, 25° C. storage.
Figure 15:
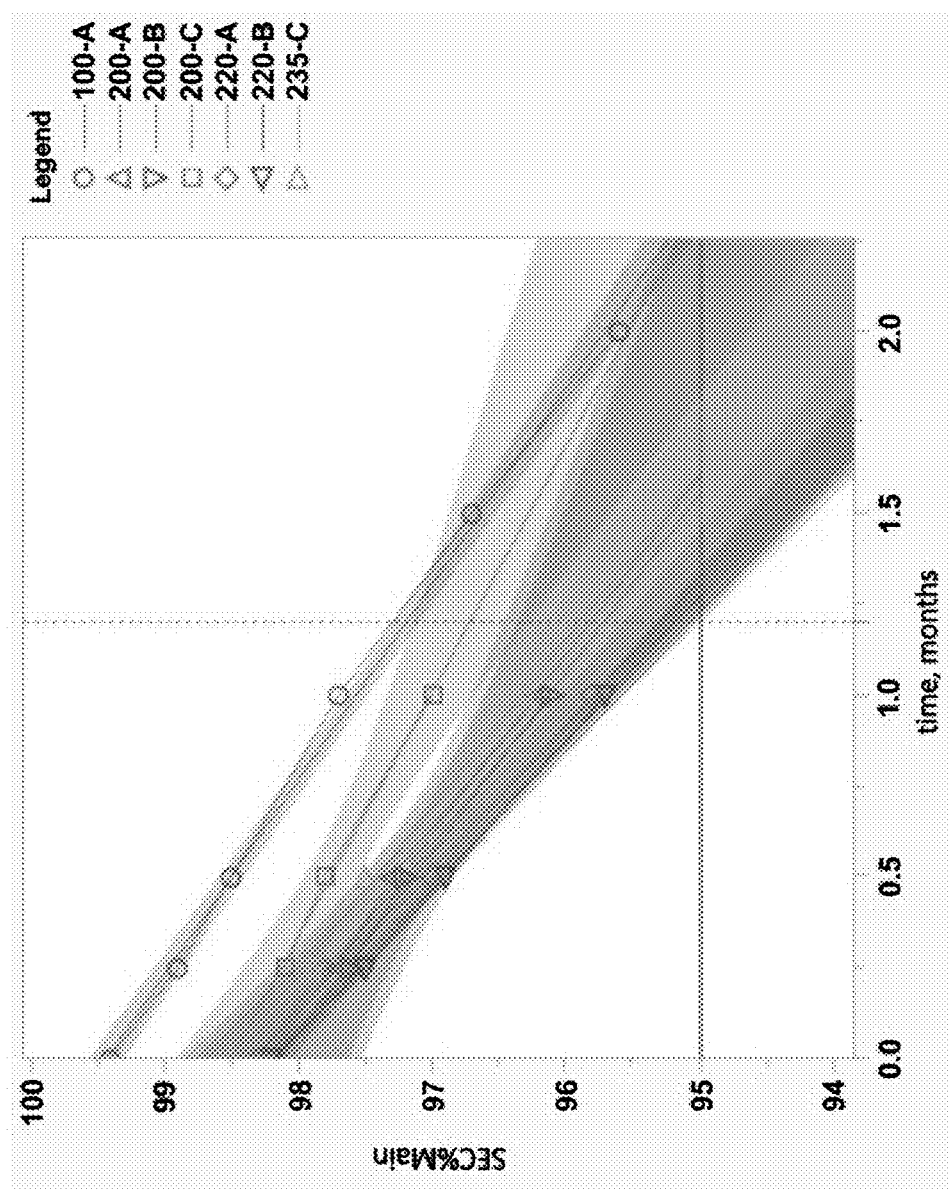
FIG. 15 is a graph showing SEC % Main as a function of time, 40° C. storage.
Figure 16:
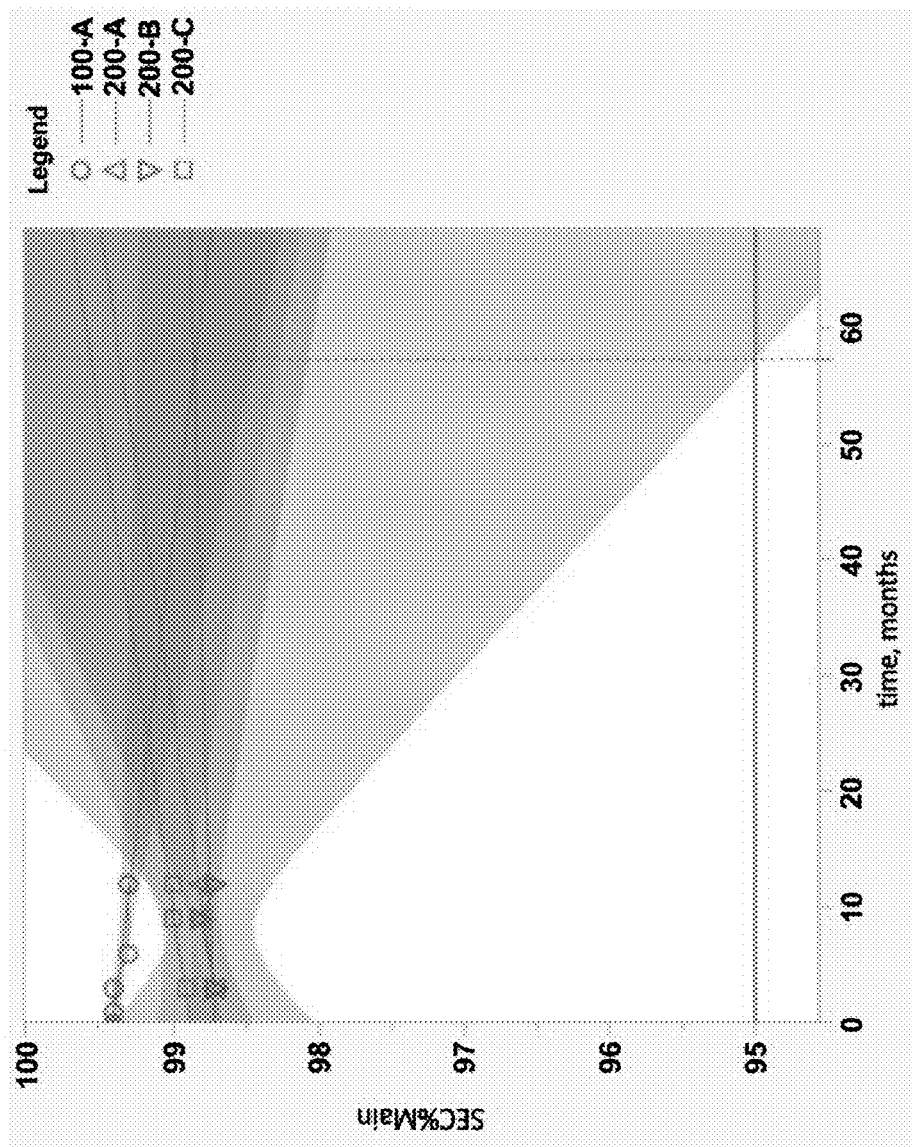
FIG. 16 is a graph showing SEC % Main as a function of time, −70° C. storage.

A statistical analysis was performed for SEC results from Formulations held at the recommended storage condition, 5° C. (FIG. 13), at accelerated storage condition, 25° C. (FIG. 14), at the stressed storage condition, 40° C. (FIG. 15), and at frozen storage condition, −70° C. (F6).

The statistical analysis assessed the Null Hypothesis (zero slope) with a one-sided 95% confidence interval; statistical significance was set at p-value<0.05 for the slope being statistically non-zero, Table 15.

KPL-404 was stable at 5° C. in the current formulation at 100 mg/mL, showing slow rate of change over 12 months with a slope that projects a ~1% change after 60 months. Of the three formulations at 200 mg/mL, Formulation C was more stable than both Formulations A and B; the slope for Formulation C predicts a ~1% change after ~36 months, whereas A and B project twice the rate of change as Formulation C. There is a sharp increase in loss of main through aggregation for all three formulations at 220 mg/mL for A and B, and 235 mg/mL for C.

Trends observed at 5° C. were recapitulated in the accelerated stress condition at 25° C., with change of % Main occurring at a similar rate for Formulation A at 100 mg/mL and Formulation C at 200 mg/mL. The stability of KPL-404 in Formulation C at 235 mg/mL is consistently more stable than Formulations A and B at 220 mg/mL, whereas at 5° C. they were essentially equivalent.

Trends observed at 40° C. mirrored trends at 25° C. and 5° C., with change of % Main occurring at a similar rate for Formulation A at 100 mg/mL and Formulation C at 200 mg/mL. Note that only Formulation A at 100 mg/mL had sufficient data for meaningful statistical analysis; analysis of higher concentration data sets are included in Table 15 for qualitative comparison, which shows Formulation C was superior to Formulations A and B at reducing aggregation when held at the stressed storage condition 40° C. The results also show that even at elevated concentrations studied here, KPL-404 is a generally stable mAb against aggregation.

KPL-404 was stable at −70° C., with change of % Main occurring at a similar rate for Formulation A at 100 mg/mL and for Formulations A, B, and C at 200 mg/mL. Note that only Formulation A at 100 mg/mL had sufficient data for meaningful statistical analysis; analysis of higher concentration data sets are included in Table 15 for qualitative comparison. The data predict no statistically meaningful change in % Main purity while held frozen, through 12 months of data.

TABLE 15

Summary of P-values for Slope of SEC Results as a Function of Time.

| Temperature | Formulation | Concentration | Slope | P-value (slope) |
|---|---|---|---|---|
| 5 C. | A | 100 mg/mL | −0.017 | 0.0809 |
| | | 200 mg/mL | −0.058 | <.0001 |
| | | 220 mg/mL | −0.114 | 0.0072 |
| | B | 200 mg/mL | −0.058 | <.0001 |
| | | 220 mg/mL | −0.034 | 0.3896 |
| | C | 200 mg/mL | −0.028 | 0.002 |
| | | 235 mg/mL | −0.071 | 0.0834 |
| 25 C. | A | 100 mg/mL | −0.171 | <.0001 |
| | | 200 mg/mL | −0.235 | <.0001 |
| | | 220 mg/mL | −0.383 | <.0001 |
| | B | 200 mg/mL | −0.23 | <.0001 |
| | | 220 mg/mL | −0.329 | <.0001 |
| | C | 200 mg/mL | −0.169 | <.0001 |
| | | 235 mg/mL | −0.275 | <.0001 |
| 40 C. | A | 100 mg/mL | −1.861 | <.0001 |
| | | 200 mg/mL | −2.029 | <.0001[1] |
| | | 220 mg/mL | −2.549 | <.0001[1] |
| | B | 200 mg/mL | −2.029 | <.0001[1] |
| | | 220 mg/mL | −2.48 | <.0001[1] |
| | C | 200 mg/mL | −1.486 | <.0001[1] |
| | | 235 mg/mL | −2.171 | <.0001[1] |
| −70 C. | A | 100 mg/mL | −0.0099 | 0.0656 |
| | | 200 mg/mL | 0.0119 | 0.1185[1] |
| | B | 200 mg/mL | 0.0024 | 0.7283[1] |
| | C | 200 mg/mL | 0.0119 | 0.1185[1] |

[1]P-value is not meaningful with fewer than 5 points, but is included for qualitative comparison In summary, KPL-404 is stable in all three formulations, but Formulation C is superior to both Formulation A and B in supporting concentrations above 200 mg/mL.

Studies were performed in three candidate formulations. KPL-404 was formulated at 200 mg/mL in each of the three candidate formulations by UF/DF and set on stability in a vial presentation.

KPL-404 was highly concentrated by UF/DF until the flux went to zero. The concentrations that were achieved were 272 and 274 mg/mL in Formulation A and B, respectively, and 291 mg/mL in Formulation C.

Samples of each of these were characterized externally using biophysical techniques available at Malvern Panalytical and at FDB.

These studies show that KPL-404 is well described by reversible monomer-dimer equilibrium below ~130 mg/mL.

At elevated concentrations from ~130 to 200 mg/mL, higher ordered reversible oligomers were formed in all three Formulations to varying degrees.

Viscosity and Instron testing were performed as a function of protein concentration to assess syringeability. Results showed Formulation C is more effective at reducing viscosity, and can support higher concentrations as compared to Formulations A and B.

Formulation C exhibits superior properties, either in a standard Yposmate autoinjector up to 235 mg/mL, or up to 270 mg/mL in the Ypsomate Pro.

All three formulations were placed on stability at 200 mg/mL, which is the upper concentration limit for Formulation A based on injectability data. Short-term (3 months) stability was also assessed at 220 mg/mL in Formulation A and B, and at 235 mg/mL in Formulation C.

Formulation C at 200 mg/mL was approximately as stable as Formulation A at 100 mg/mL.

Based all results collected, Formulation C was identified as a superior formulation, relative to Formulations A and B, for KPL-404. An upper concentration limit of 250 mg/mL can be supported for drug substance final UF/DF.

Example 2

A 26-Week Repeat-Dose Toxicity and Toxicokinetic Study of KPL-404 Administered Once Weekly Via Intravenous or Subcutaneous Injection to Cynomolgus Monkeys with an 8-Week Recovery Period The objectives of this study were to evaluate the toxicity of KPL-404 prepared in Formulation C (200 mg/mL KPL-404, 50 mM Acetate, 100 mM L-Arginine, 100 mM L-Glutamate, 0.02% polysorbate 20, pH 5.4, when administered by intravenous or subcutaneous injection once weekly over a 26-week period to cynomolgus monkeys and to evaluate the potential reversibility or delayed occurrence of any effects over an 8-week recovery period. In addition, the toxicokinetic characteristics of the test article were determined. KPL-404 was administered to 5 male and 5 female cynomolgus monkey per group via subcutaneous (SC) injection or intravenous bolus (IV) injection at doses of 30 or 97 mg/kg, once weekly for 26 weeks, according to the study design in In-text Table 1. The control article, Formulation C without KPL-404, was given by SC injection at the same dosing frequency.

TABLE 16

Experimental Design

| Group | Test Material | Route* | Dose (mg/kg) Level | Dose (mg/mL) Conc. | Dose (mL/kg) Volume | Terminal Male | Terminal Female | Recovery Male | Recovery Female |
|---|---|---|---|---|---|---|---|---|---|
| 1 | Control | SC | 0 | 0 | 0.5 | 3 | 3 | 2 | 2 |
| 2 | KPL-404 | SC | 30 | 60 | 0.5 | 3 | 3 | 2 | 2 |
| 3 | KPL-404 | SC | 97 | 194 | 0.5 | 3 | 3 | 2 | 2 |
| 4 | KPL-404 | IV | 30 | 60 | 0.5 | 3 | 3 | 2 | 2 |
| 5 | KPL-404 | IV | 97 | 194 | 0.5 | 3 | 3 | 2 | 2 |

*SC = Subcutaneous;
IV = Intravenous

Toxicology Results

No unexpected adverse effects were observed in cynomolgus monkeys treated with placebo, or with either the low 30 mg/kg or high doses 97 mg/kg dose levels of KPL-404 in Formulation C; all effects observed were attributable to the pharmacological action of KPL-404.

CONCLUSION

KPL-404 is stable in all three formulations, but Formulation C is superior to both Formulation A and B in providing stable formulations of KPL-404, and Formulation C was further demonstrated to be safe in non-human primate toxicity studies.

Other Embodiments

While specific aspects of the invention have been described and illustrated, such aspects should be considered illustrative of the invention only and not as limiting the invention as construed in accordance with the accompanying claims. All publications and patent applications cited in this specification are herein incorporated by reference in their entirety for all purposes as if each individual publication or patent application were specifically and individually indicated to be incorporated by reference for all purposes. Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

The invention claimed is:

1. A pharmaceutical composition formulated for intravenous injection comprising 200 mg/ml of an anti-CD40 antibody or antigen-binding fragment thereof comprising a heavy chain comprising the amino acid sequence set forth in SEQ ID NO: 1, and a light chain comprising the amino acid sequence set forth in SEQ ID NO: 2, wherein the pharmaceutical composition comprises 0.02% polysorbate 20, 50 mM sodium acetate, 100 mM arginine, and 100 mM glutamate, a pH of 5.4.

2. The pharmaceutical composition of claim 1, wherein the pharmaceutical composition is present in a volume of 2.0 mL.

3. A pharmaceutical composition formulated for subcutaneous injection comprising 200 mg/ml of an anti-CD40 antibody or antigen-binding fragment thereof comprising a heavy chain comprising the amino acid sequence set forth in SEQ ID NO: 1, and a light chain comprising the amino acid sequence set forth in SEQ ID NO: 2, wherein the pharmaceutical composition comprises 0.02% polysorbate 20, 50 mM sodium acetate, 100 mM arginine, and 100 mM glutamate, a pH of 5.4.

4. The pharmaceutical composition of claim 3, wherein the pharmaceutical composition is present in a volume of 2.0 mL.

5. A method of suppressing the immune system in a human subject comprising administering to the human subject by intravenous injection a pharmaceutical composition comprising 200 mg/ml of an anti-CD40 antibody or antigen-binding fragment thereof comprising a heavy chain comprising the amino acid sequence set forth in SEQ ID NO: 1, and a light chain comprising the amino acid sequence set forth in SEQ ID NO: 2, wherein the pharmaceutical composition comprises 0.02% polysorbate 20, 50 mM sodium acetate, 100 mM arginine, and 100 mM glutamate, a pH of 5.4.

6. The method of claim 5, wherein the pharmaceutical composition is present in a volume of 2.0 mL.

7. A method of suppressing the immune system in a human subject comprising administering to the human subject by subcutaneous injection a pharmaceutical composition comprising 200 mg/ml of an anti-CD40 antibody or antigen-binding fragment thereof comprising a heavy chain comprising the amino acid sequence set forth in SEQ ID NO: 1, and a light chain comprising the amino acid sequence set forth in SEQ ID NO: 2, wherein the pharmaceutical composition comprises 0.02% polysorbate 20, 50 mM sodium acetate, 100 mM arginine, and 100 mM glutamate, a pH of 5.4.

8. The method of claim 7, wherein the pharmaceutical composition is present in a volume of 2.0 mL.

* * * * *